US008236765B2

(12) United States Patent
Yu et al.

(10) Patent No.: US 8,236,765 B2
(45) Date of Patent: Aug. 7, 2012

(54) GANGLIOSIDE EPITOPES FOR TREATING GUILLAIN-BARRE SYNDROME

(75) Inventors: Robert Yu, North Augusta, SC (US); Seigo Usuki, Augusta, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 79 days.

(21) Appl. No.: 12/789,193

(22) Filed: May 27, 2010

(65) Prior Publication Data

US 2011/0131669 A1      Jun. 2, 2011

Related U.S. Application Data

(60) Provisional application No. 61/274,434, filed on Aug. 18, 2009, provisional application No. 61/277,297, filed on Sep. 24, 2009.

(51) Int. Cl.
*A61K 38/00* (2006.01)
*A61K 39/395* (2006.01)
(52) U.S. Cl. ..... 514/18.2; 514/8.3; 514/17.7; 424/130.1
(58) Field of Classification Search ........................ None
See application file for complete search history.

(56) References Cited

U.S. PATENT DOCUMENTS 5,529,922 A      6/1996 Chapman

FOREIGN PATENT DOCUMENTS

EP      1279677      1/2003

OTHER PUBLICATIONS

Andersen, et al., "Inability of insulin to maintain normal nerve function during high-frequency stimulation in diabetic rat tail nerves", Muscle Nerve 17:80-84 (1994).
Ariga and Yu, "Antiglycolipid antibodies in Guillain-Barré syndrome and related diseases: review of clinical features and antibody specificities", J. Neurosci. Res, 80:1-17 (2005).
Barrett, et al., "Postural effects on peritoneal transport and systemic uptake of radiolabeled monoclonal antibodies", Cancer Immunol Immunother 44:173-178 (1997).
Birren and Wall, "Age changes in conduction velocity, refractory period, number of fibers, connective tissue space and blood vessels in sciatic nerve of rats", J Comp Neurol., 104:1-16 (1956).
Buchwald, et al., "Intravenous immunoglobulins neutralize blocking antibodies in Guillain-Barré syndrome", Ann Neurol., 51:673-680 (2002).
Chapman, et al., "A phase II trial comparing five dose levels of BEC2 anti-idiotypic monoclonal antibody vaccine that mimics GD3 gangliosde", Vaccine, Elsevier Ltd, 22(21):2904-2909 (2004).
Dalakas, "Blockade of blocking antibodies in Guillain-Barré syndromes: "unblocking" the mystery of action of intravenous immunoglobulin", Annals of Neurology, 51(6):667-69 (2002).
Guex and Putsch, "Swiss-Model and the Swiss-PdbViewer: an environment for comparative protein modeling", Electrophoresis 18:2714-2723 (1997).

Jones and Roberts, "The quantiative measurement of motor incoordination in naive mice using an acelerating rotarod", J. Pharm. Pharmacol., 20:302-304 (1968).
Kaida, et al., "Antiganglioside antibodies and their pathophysiological effects on Guillain-Barré syndrome and related disorders—a review", Glycobiology 19: 676-692 (2009).
Kaida, et al., "Anti-ganglioside complex antibodies associated with severe disability in GBS", J. Neuroimmunol. 182:212-218 (2009).
Kieseier, et al., "intravenous immunoglobulins in the treatment of immune neuropathies", Curr Opin Neurol., 21:555-562 (2008).
McCaffery, et al., "Immunization of melanoma patients with BEC2 anti-idiotypic monoclonal antibody that mimics GD3 ganglioside: enhanced immunogenicity when combined with adjuvant", Clinical Cancer Res., 2(4):679-686 (1996).
Nasi, et al, "Anti-melanoma effects of R24, a monoclonal antibody against GD3 ganglioside", Melanoma Research, 7(2):S155-S162 (1997).
Popa, et al., "GD3-replica peptides selected from a phage peptide library induce a GD3 ganglioside antibody response", FEBS Lett., 580:1398-1404 (2006).
Ren, et al., "O-acetylated gangliosides in bovine buttermilk. Characterization of 7-O-acetyl, 9-O-acetyl, and 7,9-di-O-acetyl GD3", J. Biol. Chem. 267:12632-12638 (1992).
Rinaldi and Willison, "Ganglioside antibodies and neuropathies", Curr Opin Neurol 21:540-546 (2008).
Rogers, et al., "Correlation between motor impairment and infarct volume after permanent and transient middle cerebral artery occlusion in the rat", Stroke 28:2060-66 (1997).
Todeschini and Hakomori, "Functional role of glycosphingolipids and gangliosides in control of cell adhesion, motility, and growth, through glycosynaptic microdomains", Biochim. Biophys. Acta., 1780:421-433 (2008).
Usuki et al., "AIDP and CIDP having specific antibodies to the carbohydraste epitope", .J. Neurol. Sci.,. 232:37-44 (2005).
Usuki, et al.,"Molecular mimicry sensitization of Lewis rats with *Campylobacter jejuni* lipopolysaccharides induces formation of antibody toward GD3 ganglioside", J Neurosci Res., 83:274-284 (2006).
Usuki, et al., "Novel anti-idiotype antibody therapy for Lipooligosaccharide-induced experimental autoimmune neuritis: use relevant to Guillain-Barré syndrome", J. Neurosci. Res., 88(8):1651-1663 (2010).
Usuki, et al., "Development of a nocel therapy for Lipo-oligosaccharide-induced experimental neuritis:use of peptide glycomimics", J Neurochem., 113(2):351-362 (2010).
Usuki, et al., "Chemical validation of molecular mimicry: interaction of cholera toxin with *Campylobacter* lipooligosaccharides", Glycoconj J., 24:167-180 (2007).
van Doorn, et al., "Clinical features, pathogenesis, and treatment of Guillain-Barré syndrome", Lancet Neurol 7:939-950 (2008).

(Continued)

*Primary Examiner* — Olga N Chernyshev
(74) *Attorney, Agent, or Firm* — Pabst Patent Group LLP

(57) ABSTRACT

Disclosed are compositions and methods for treating Guillain-Barré syndrome (GBS) in a subject that involves neutralizing specific pathogenic anti-glycolipid antibodies in the circulation of the subject. This can involve administering to the subject a molecular mimic of a ganglioside that serves as a specific competitive inhibitor for anti-ganglioside antibodies in the circulation. Also disclosed is an animal model of GBS having anti-ganglioside antibodies in the circulation.

3 Claims, 18 Drawing Sheets

OTHER PUBLICATIONS

Wahl, et al., "The intraperitoneal delivery of radiolabeled monoclonal antibodies: studies on the regional delivery advantage", Cancer Immunol Immunother 26: 187-201 (1988).

Willers, at al., "Molecular mimicry of phage displayed peptides mimicking GD3 ganglioside", Peptides, 20:1021-1026 (1999).

Willison, "The immunobiology of Guillain-Barré syndromes", J. of the Peripheral Nervous System, 10(2):94-112 (2005).

Yu, et al., "Regulation of ganglioside biosynthesis in the nervous system", J. Lipid Res. 45:783-793 (2004).

Zhang, et al., "Anti-ganglioside antibody-mediated neuronal cytotoxicity and its protection by intravenous immunoglobulin: implications for immune neuropathies", Brain Oxford University Press, 127(5):1085-1100 (2004).

Yang, L., Nolan, J.P., "High-Throughput Screening and Characterization of Clones Selected form Phage Display Libraries," Cytometry, 71A:625-631, 2007.

Qiu, J., Marcus D.M., "Use of peptide ligands to analyse the fine specificity of antibodies against asialo GM1," J. of Neuroimmunology, 100:58-63, 1999.

Qiu, J., et al., "Stucture-function studies of an anti-asialo GM1 antibody obtained from a phage display library," J. of Neuroimmunolony, 97:172-181, 1999.

SEQUENCE LISTING

```
<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: Synthetic Construct

<400> SEQUENCE: 1

Leu Ala Pro Pro Arg Pro Arg Ser Glu Leu Val Phe Leu Ser Val
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic Construct

<400> SEQUENCE: 2

Pro His Phe Asp Ser Leu Leu Tyr Pro Cys Glu Leu Leu Gly Cys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic Construct

<400> SEQUENCE: 3

Gly Leu Ala Pro Pro Asp Tyr Ala Glu Arg Phe Phe Leu Ile Ser
1               5                   10                  15

<210> SEQ ID NO 4
```

```
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Arg His Ala Tyr Arg Ser Met Ala Glu Trp Gly Phe Leu Tyr Ser
1               5                   10                  15

<210> SEQ ID NO 5
<211> LENGTH: 12
<212> TYPE: PRT
<213> ORGANISM: Artificial Sequence
<220> FEATURE:
<223> OTHER INFORMATION: Synthetic Construct

<400> SEQUENCE: 5

Ala Cys Thr Pro Tyr Ala Met Leu Pro Gly Cys Lys
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic Construct

<400> SEQUENCE: 6

Ser Val Ala Val Pro Pro Pro Ala Asp Asp Pro Ser Trp Arg Tyr
1               5                   10                  15
```

GANGLIOSIDE EPITOPES FOR TREATING GUILLAIN-BARRE SYNDROME

CROSS REFERENCE TO RELATED APPLICATIONS

This application claims benefit of U.S. Provisional Application No. 61/274,434, filed Aug. 18, 2009 and U.S. Provisional Application No. 61/277,297, filed Sep. 24, 2009, which are hereby incorporated herein by reference in their entirety.

STATEMENT REGARDING FEDERALLY SPONSORED RESEARCH OR DEVELOPMENT

This invention was made with Government Support under Agreement NS26994-20 awarded by the National Institutes of Health. The Government has certain rights in the invention.

FIELD OF THE INVENTION

The invention is generally related to autoantibody neutralization, more particularly to polypeptides and proteins for treating Guillain-Barré syndrome.

BACKGROUND OF THE INVENTION

Guillain-Barré syndrome (GBS) is an immune-mediated disorder of the peripheral nervous system characterized by neuromuscular weakness and frequently accompanied by flaccid paralysis and may occasionally lead to death. It is classified as an acute inflammatory demyelinating polyneuropathy with a variant form designated as acute motor axonal neuropathy (Hughes and Cornblath, 2005. *Lancet* 366:1653-1666). Anti-ganglioside antibodies have been proposed as contributors to GBS pathogenesis (Kaida et al., 2009. *J. Neuroimmunol.* 182:212-218; Ariga and Yu, 2005. *J. Neurosci. Res.* 80:1-17). Gangliosides are abundantly expressed in human nerves (Yu et al., 2004. *J. Lipid Res.* 45:783-793) and generally believed to have important roles as mediators of cell adhesion and modulators of signal transduction (Regina Todeschini and Hakomori 2008. *Biochim. Biophys. Acta* 1780:421-433).

The etiology of GBS is complex and not fully known. A growing body of evidence, however, indicates that aberrant immune responses triggered by an infectious agent or vaccination allow disease development and the underlying pathogenetic mechanisms (Langmuir et al., 1984. *Am J Epidemiol* 119: 841-879; Kuwabara, 2004. *Drugs* 64: 597-610; Souayah et al., 2007. *Vaccine* 25: 5253-5255). The most commonly identified microbial agents are *Campylobacter jejuni* (*C. jejuni*), *Haemophilus influenzae*, cytomegalovirus (CMV), Epstein-Barr virus, and *Mycoplasma pneumoniae* (Hughes et al., 1999. *J Neuroimmunol* 100: 74-97; Hadden et al., 2001. *Neurology* 56: 758-765; Sivadon-Tardy et al., 2006. *Emerg Infect Dis* 12: 990-993; Sivadon-Tardy et al., 2009. *Clin Infect Dis* 48: 48-56). A preceding infectious event and patient-related host factors also seem to be related to certain subtypes of GBS and may affect the severity of the disease (Geleijns et al., 2005. *Neurology* 64: 44-49; Caporale et al., 2006. *J Neuroimmunol* 177: 112-118; Yuki, 2007. *Muscle Nerve* 35: 691-711). *C. jejuni* infection frequently induces anti-ganglioside antibodies in the patient's serum (Yuki et al., 1990. *Neurology* 40: 1900-1902; Usuki et al., 2006. *J Neurosci Res* 83: 274-284). Thus, despite the possibility of other pathogenic mechanisms, an antibody-mediated process is one of the major insults to the nerve, causing both conduction block and velocity loss and the ensuing clinical symptoms (Rinaldi and Willison, 2008. *Curr Opin Neurol* 21: 540-546; van Doorn et al., 2008. *Lancet Neural* 7: 939-950; Kaida et al., 2009. *Glycobiology* 19: 676-692).

Conventional treatment strategies rely heavily on removal of pathogenic anti-glycolipid antibodies from the blood circulation. In practice, plasmapheresis and intravenous immunoglobulin (IVIG) have been used extensively for treatment (Buchwald et al, 2002. *Ann Neurol* 51: 673-680; Kieseier et al., 2008. *Curr Opin Neurol* 21: 555-562). Both strategies, however, are invasive and remove both nonpathogenic and pathogenic antibodies from circulation, with attendant risk of undesirable side effects.

It is an object of the invention to provide a methods and compositions for treating GBS with minimal or no side effects.

SUMMARY OF THE INVENTION

Disclosed are compositions and methods for treating Guillain-Barré syndrome (GBS) in a subject that involves neutralizing specific pathogenic anti-glycolipid antibodies in the circulation of the subject. This can involve administering to the subject a ganglioside molecular mimic that serves as a specific competitive inhibitor for anti-ganglioside antibodies in the circulation. The molecular mimic can be a polypeptide having a ganglioside epitope. The molecular mimic can be an anti-idiotypic antibody for the ganglioside. Also disclosed is an animal model of GBS having anti-ganglioside antibodies in the circulation.

BRIEF DESCRIPTION OF THE DRAWINGS

(FIG. 6C) as a function of time (min). The arrows show addition of the serum and washing out.

DETAILED DESCRIPTION OF THE INVENTION

Methods of Treating Guillain-Barré Syndrome

Figure 1:
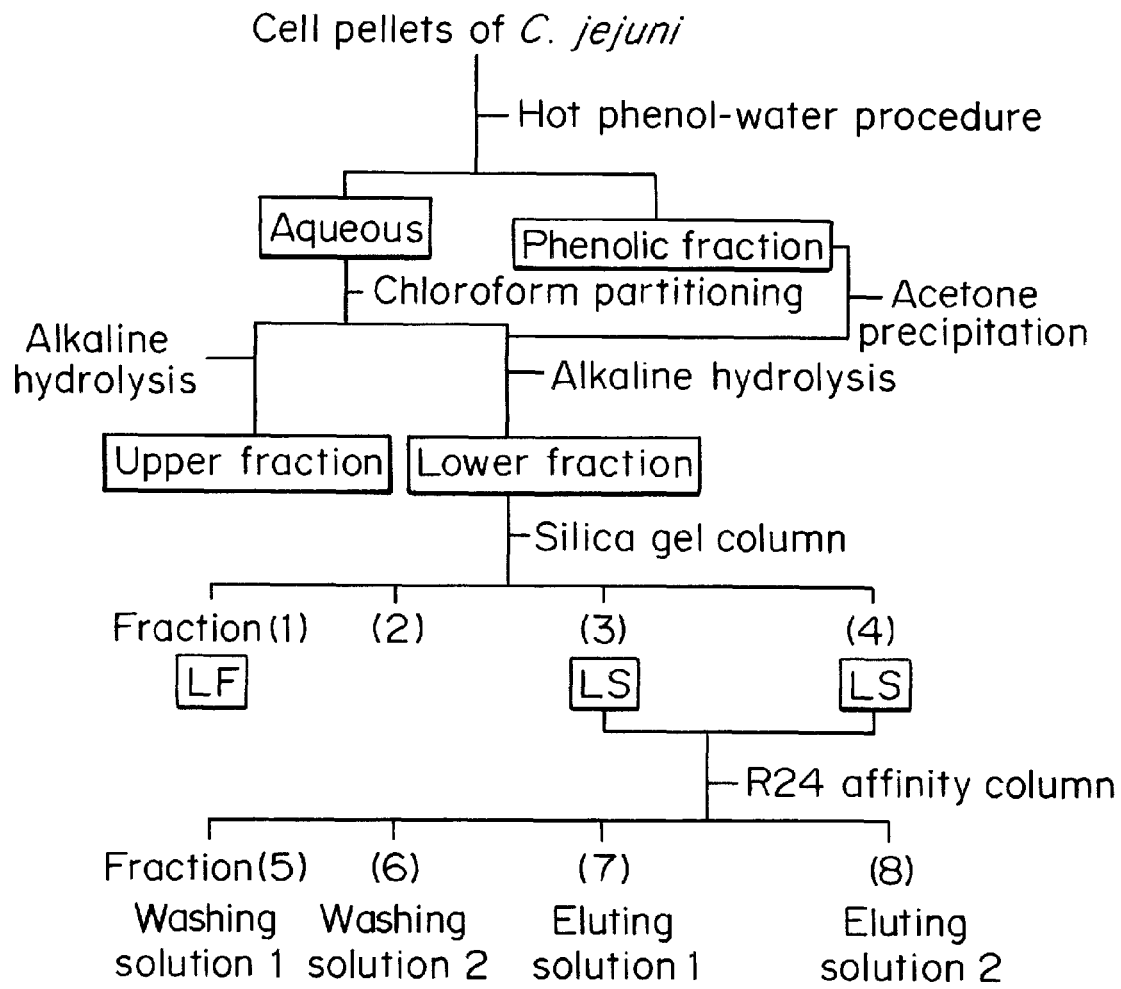
FIG. 1 is a diagram showing the scheme for isolating from a crude lipooligosaccharide (LOS) fraction a GD3 ganglioside-like LOS ($LOS_{GD3}$).

Guillain-Barré syndrome (GBS) is an acute inflammatory demyelinating polyneuropathy with a variant form designated as acute motor axonal neuropathy. Anti-ganglioside antibodies contribute to this pathogenesis. Gangliosides are abundantly expressed in human nerves and have important roles as mediators of cell adhesion and modulators of signal transduction. Molecular mimicry between microbial lipooligosaccharide (LOS) antigens and endogenous ganglioside GM1 has been proposed as an etiological mechanism for GBS because of the findings that the autoantibodies for GM1 [Galβ1-3GalNAcβ1-4(NeuAcα2-3)Galβ1-4Glcβ1-1'Cer] can often be elicited by preceding infections by *Campylobacter jejuni*. Moreover, elevated titers of circulating antibodies to GD3 ganglioside [NeuAcα2-8NeuAcα2-3Galβ1-4Glcβ1-1'Cer] occur in some patients with inflammatory demyelinating polyneuropathies. Specifically, a $LOS_{GD3}$ antigen having the tetrasaccharide epitope [NeuAc-NeuAc-Gal-Hep] was identified in strain HS19 of *C. jejuni*.

Conventional treatment strategies rely heavily on removal of pathogenic anti-glycolipid antibodies from the blood circulation. In practice, plasmapheresis and intravenous immunoglobulin (IVIG) have been used extensively for treatment. Both strategies, however, are invasive and remove both non-pathogenic and pathogenic antibodies from circulation, with attendant risk of undesirable side effects.

For this reason, a method is disclosed that involves neutralizing specific pathogenic anti-glycolipid antibodies in the circulation of the subject. This can involve administering to the subject a molecular mimic of one or more gangliosides, such as GM1, GQ1b, and GD3, that serves as a specific competitive inhibitor for anti-ganglioside antibodies in the circulation.

Therefore, a method is provided for treating GBS in a subject. The method can involve administering to the subject an effective amount of a pharmaceutical composition having a polypeptide having a gangliosides epitope. The method can involve administering to the subject an effective amount of a pharmaceutical composition having a polypeptide having a GD3 epitope. The method can involve administering to the subject an effective amount of a pharmaceutical composition having a polypeptide having a GQ1b epitope. The method can involve administering to the subject an effective amount of a pharmaceutical composition having a polypeptide having a GM1 epitope.

As used herein, "ganglioside epitope" refers to any molecule mimicking a ganglioside such that antibodies that specifically bind the ganglioside will also specifically bind the ganglioside epitope. For example, "GD3 epitope" refers to any molecule mimicking GD3 ganglioside such that antibodies that specifically bind GD3 will also specifically bind the GD3 epitope. GD3 is a ganglioside. Thus, the polypeptide having the GD3 epitope is not native GD3. Thus, in some embodiments, antibodies specific for the GD3 ganglioside NeuAcα2-8NeuAcα2-3Galβ1-4Glcβ1-1'Cer will also specifically bind the polypeptide having the GD3 epitope.

Polypeptides

GD3 Polypeptides

In some embodiments, the polypeptide having the GD3 epitope has an amino acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence SEQ ID NO:3, SEQ ID NO:4, SEQ ID NO:5, or SEQ ID NO:6.

In some embodiments, any change from the amino acid sequence SEQ ID NO:3, SEQ ID NO:4, SEQ ID NO:5, or SEQ ID NO:6 is a conservative variation.

Thus, the polypeptide having the GD3 epitope can include the amino acid sequence SEQ ID NO:3, SEQ ID NO:4, SEQ ID NO:5, SEQ ID NO:6, or a conservative variant thereof.

In some embodiments, the polypeptide having the GD3 epitope can be at least 8, 9, 10, 11, 12, 13, 14 amino acids in length. In some embodiments, the polypeptide having the GD3 epitope can be less than 20, 25, 30, 35, 40, 45, 50, 60, 70, 80, 90, 100 amino acids in length.

GM1 Polypeptides

Polypeptides can also be identified and produced that contain the GM1 epitope. For example, GM1 protein fragments can be screened using anti-GM1 antibodies from *C. jejuni*. Alternatively, peptide libraries can be screened for binding by anti-GM1 antibodies from *C. jejuni*. Once the sequence of the polypeptides containing the GM1 epitope is identified, polypeptides can be produced containing an amino acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence identified in the polypeptide having the GM1 epitope.

GQ1b Polypeptides

Polypeptides can also be identified and produced that contain the GQ1b epitope. For example, GQ1b protein fragments can be screened using anti-GQ1b antibodies from, for example, *C. jejuni*. Alternatively, peptide libraries can be screened for binding by anti-GQ1b antibodies from *C. jejuni*. Once the sequence of the polypeptides containing the GQ1b epitope is identified, polypeptides can be produced containing an amino acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence identified in the polypeptide having the GQ1b epitope.

Anti-Idiotype Antibodies

In some embodiments, the polypeptide having the ganglioside epitope is an anti-idiotypic antibody that specifically binds one or more idiotopes within the paratope of an anti-ganglioside antibody. A "paratope" is the part of an antibody is the site within an immunoglobuline Fab that specifically interacts with the epitope of the antigen. An "idiotope" is an antigenic determinant (epitope) within the variable region of the immunoglobulin product of a clone. Thus, idiotopes are epitopes to which an anti-idiotype antibody binds. The paratope of the anti-idiotypic antibody contains a mirror image of the original antibody's paratope, which is a mirror image of the antigen's epitope. Consequently, the anti-idiotypic antibody contains a three-dimensional binding site that mimics the structure of the original antigen.

Thus, disclosed is an anti-idiotypic antibody containing a paratope having a molecular mimic of a GM1, GQ1b, or GD3 epitope.

BEC2 Anti-Idiotypic Antibody GD3

U.S. Pat. No. 5,529,922 by Chapman et al. is incorporated by reference herein in its entirety for its disclosure of an anti-idiotypic monoclonal antibody that induces an immune response against the ganglioside GD3 and specifically binds to the binding site of the R24 antibody. This antibody, referred to as BEC, has a paratope that mimics the GD3 ganglioside. Thus, the polypeptide having the GD3 epitope can be the anti-idiotypic antibody designated BEC2.

According to Chapman et al., GD3 is abundantly expressed on most melanomas but is expressed only to a limited extent and at a low concentration on normal tissues. Thus, Chapman et al. disclose the use of the BEC2 antibody as vaccine to induce an immune response that results in an increase in circulatory anti-GD3 antibodies that will target melanomas.

Disclosed is an alternative use of the anti-idiotypic antibody for GD3 to neutralize circulating anti-GD3 antibodies in patients with GBS.

Antibodies Generally

The term "antibody" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with anti-GD3 antibodies such that anti-GD3 antibodies is inhibited from interacting with GD3. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The term "antibody" as used herein is meant to include intact molecules as well as fragments thereof, such as, for example, Fab and $F(ab')_2$, which are capable of binding the epitopic determinant.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

Combination Therapies

In some embodiments, the method further involves administering to the subject a second therapeutic substance that can be administered to a subject having GBS to treat one or more symptoms associated with GBS. For example, the provided composition(s) can further include one or more of classes of antibiotics (e.g., Aminoglycosides, Cephalosporins, Chloramphenicol, Clindamycin, Erythromycins, Fluoroquinolones, Macrolides, Azolides, Metronidazole, Penicillins, Tetracyclines, Trimethoprim-sulfamethoxazole, Vancomycin), steroids (e.g., Andranes (e.g., Testosterone), Cholestanes (e.g., Cholesterol), Cholic acids (e.g., Cholic acid), Corticosteroids (e.g., Dexamethasone), Estraenes (e.g., Estradiol), Pregnanes (e.g., Progesterone), narcotic and non-narcotic analgesics (e.g., Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), anti-inflammatory agents (e.g., Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Momiflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflumate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triclonide, Triflumidate, Zidometacin, Zomepirac Sodium), or anti-histaminic agents (e.g., Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

The disclosed compositions and methods involve reducing circulating antibodies against GD3. However, GD3 is expressed on melanoma cells, and thus immune response against GD3 is beneficial to treat or prevent melanoma. Thus, in some embodiments, the disclosed method further involves administering to the subject an anti-cancer (antineoplastic) drug. Antineoplastic drugs include Acivicin, Aclarubicin, Acodazole Hydrochloride, AcrQnine, Adozelesin, Aldesleukin, Altretamine, Ambomycin, Ametantrone Acetate, Aminoglutethimide, Amsacrine, Anastrozole, Anthramycin, Asparaginase, Asperlin, Azacitidine, Azetepa, Azotomycin, Batimastat, Benzodepa, Bicalutamide, Bisantrene Hydrochloride, Bisnafide Dimesylate, Bizelesin, Bleomycin Sulfate, Brequinar Sodium, Bropirimine, Busulfan, Cactinomycin, Calusterone, Caracemide, Carbetimer, Carboplatin, Carmustine, Carubicin Hydrochloride, Carzelesin, Cedefingol, Chlorambucil, Cirolemycin, Cisplatin, Cladribine, Crisnatol Mesylate, Cyclophosphamide, Cytarabine, Dacarbazine, Dactinomycin, Daunorubicin Hydrochloride, Decitabine, Dexormaplatin, Dezaguanine, Dezaguanine Mesylate, Diaziquone, Docetaxel, Doxorubicin, Doxorubicin Hydrochloride, Droloxifene, Droloxifene Citrate, Dromostanolone Propionate, Duazomycin, Edatrexate, Eflomithine Hydrochloride, Elsamitrucin, Enloplatin, Enpromate, Epipropidine, Epirubicin Hydrochloride, Erbulozole, Esorubicin Hydrochloride, Estramustine, Estramustine Phosphate Sodium, Etanidazole, Ethiodized Oil I 131, Etoposide, Etoposide Phosphate, Etoprine, Fadrozole Hydrochloride, Fazarabine, Fenretinide, Floxuridine, Fludarabine Phosphate, Fluorouracil, Fluorocitabine, Fosquidone, Fostriecin Sodium, Gemcitabine, Gemcitabine Hydrochloride, Gold Au 198, Hydroxyurea, Idarubicin Hydrochloride, Ifosfamide, Ilmofosine, Interferon Alfa-2a, Interferon Alfa-2b, Interferon Alfa-n1, Interferon Alfa-n3, Interferon Beta-I a, Interferon Gamma-Ib, Iproplatin, Irinotecan Hydrochloride, Lanreotide Acetate, Letrozole, Leuprolide Acetate, Liarozole Hydrochloride, Lometrexol Sodium, Lomustine, Losoxantrone Hydrochloride, Masoprocol, Maytansine, Mechlorethamine Hydrochloride, Megestrol Acetate, Melengestrol Acetate, Melphalan, Menogaril, Mercaptopurine, Methotrexate, Methotrexate Sodium, Metoprine, Meturedepa, Mitindomide, Mitocarcin, Mitocromin, Mitogillin, Mitomalcin, Mitomycin, Mitosper, Mitotane, Mitoxantrone Hydrochloride, Mycophenolic Acid, Nocodazole, Nogalamycin, Ormaplatin, Oxisuran, Paclitaxel, Pegaspargase, Peliomycin, Pentamustine, Peplomycin Sulfate, Perfosfamide, Pipobroman, Piposulfan, Piroxantrone Hydrochloride, Plicamycin, Plomestane, Porfimer Sodium, Porfiromycin, Prednimustine, Procarbazine Hydrochloride, Puromycin, Puromycin Hydrochloride, Pyrazofurin, Riboprine, Rogletimide, Safmgol, Safingol Hydrochloride, Semustine, Simtrazene, Sparfosate Sodium, Sparsomycin, Spirogermanium Hydrochloride, Spiromustine, Spiroplatin, Streptonigrin, Streptozocin, Strontium Chloride Sr 89, Sulofenur, Talisomycin, Taxane, Taxoid, Tecogalan Sodium, Tegafur, Teloxantrone Hydrochloride, Temoporfin, Teniposide, Teroxirone, Testolactone, Thiamiprine, Thioguanine, Thiotepa, Tiazofurin, Tirapazamine, Topotecan Hydrochloride, Toremifene Citrate, Trestolone Acetate, Triciribine Phosphate, Trimetrexate, Trimetrexate Glucuronate, Triptorelin, Tubulozole Hydrochloride, Uracil Mustard, Uredepa, Vapreotide, Verteporfin, Vinblastine Sulfate, Vincristine Sulfate, Vindesine, Vindesine Sulfate, Vinepidine Sulfate, Vinglycinate Sulfate, Vinleurosine Sulfate, Vinorelbine Tartrate, Vinrosidine Sulfate, Vinzolidine Sulfate, Vorozole, Zeniplatin, Zinostatin, Zorubicin Hydrochloride.

Administration

The disclosed compounds and compositions can be administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

For oral administration, solid dosage forms of tablets, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The peptides can also be in micro-encapsulated form, if appropriate, with one or more excipients.

Parenteral administration of the composition is generally characterized by injection. Injectables can be prepared in conventional forms, either as liquid solutions or suspensions, solid forms suitable for solution of suspension in liquid prior to injection, or as emulsions. Parenteral administration can involve the use of a slow release or sustained release system such that a constant dosage is maintained.

The compositions can also be administered intranasally. As used herein, "topical intranasal administration" means delivery of the compositions into the nose and nasal passages through one or both of the nares and can involve delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

The exact amount of the compositions required can vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Generally, the dosage can vary with the age, condition, sex and extent of the disease in the patient, route of administration, or whether other drugs are included in the regimen, and can be determined by one of skill in the art. The dosage can be adjusted by the individual physician in the event of any counter indications. Guidance can be found in the literature for appropriate dosages for given classes of pharmaceutical products.

For example, a typical daily dosage of a polypeptide having a ganglioside epitope used alone might range from about 1 µg/kg to up to 100 mg/kg of body weight or more per day, depending on the factors mentioned above. For example dosages can be about 0.01 to 5 mg/kg of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg body weight.

Dosage can vary, and can be administered in one or more dose administrations daily, for one or several days. An exemplary treatment regime entails administration twice per day, once per day, once per week, once every two weeks, once every three weeks, once every four weeks, once a month, once every 3 months or once every three to 6 months.

The compositions disclosed herein can be administered prophylactically to patients or subjects who are at risk for GBS or who have been newly diagnosed with GBS.

Pharmaceutical Compositions

Also disclosed is a pharmaceutical composition for use in treating one or more symptoms of GBS. The pharmaceutical composition can include any polypeptide disclosed herein in a pharmaceutically acceptable excipient. The pharmaceutical composition can include an idiotypic antibody for a ganglioside in a pharmaceutically acceptable excipient. The pharmaceutical composition can include an amino acid sequence at least 90% identical to the amino acid sequence SEQ ID NO:3, SEQ ID NO:4, SEQ ID NO:5, or SEQ ID NO:6.

Polypeptides

Also disclosed is an isolated GD3-like polypeptide. The term "GD3-like" is used to refer to polypeptides that mimic the epitope of GD3 ganglioside. Thus, GD3-like polypeptides can have a GD3 epitope.

Also disclosed is an isolated GM1-like polypeptide. The term "GM1-like" is used to refer to polypeptides that mimic the epitope of GM1 ganglioside. Thus, GM1-like polypeptides can have a GM1 epitope.

Also disclosed is an isolated GQ1b-like polypeptide. The term "GQ1b-like" is used to refer to polypeptides that mimic the epitope of GM1 ganglioside. Thus, GQ1b-like polypeptides can have a GQ1b epitope.

In some embodiments, the disclosed polypeptide has an amino acid sequence at least 90% identical to the amino acid sequence SEQ ID NO:3, SEQ ID NO:4, SEQ ID NO:5, or SEQ ID NO:6. In some embodiments, the polypeptide includes a conservative substitution of SEQ ID NO:3, SEQ ID NO:4, SEQ ID NO:5, or SEQ ID NO:6. In preferred embodiments, the isolated polypeptide has the amino acid sequence SEQ ID NO:4.

Protein Variants

Also disclosed are functional variants of the disclosed polypeptides. The term "variant" refers to an amino acid or peptide sequence having conservative and non-conservative amino acid substitutions, insertions or deletions. Substitutions, deletions, insertions or any combination thereof may be combined to arrive at a final polypeptide.

"Functional variants" of the disclosed polypeptide include those that inhibit anti-ganglioside antibody binding to the ganglioside, for example those that inhibit anti-GD3 antibody binding to GD3 ganglioside.

Insertions include amino and/or carboxyl terminal fusions as well as intra-sequence insertions of single or multiple amino acid residues. Insertions ordinarily will be smaller insertions than those of amino or carboxyl terminal fusions, for example, on the order of one to four residues.

Deletions are characterized by the removal of one or more amino acid residues from the protein sequence. Thus, the polypeptide can have 1, 2, 3, or 4 deletions from SEQ ID NO:1, 2, 3, 4, 5, or 6. These variants ordinarily are prepared by site specific mutagenesis of nucleotides in the DNA encoding the protein, thereby producing DNA encoding the variant, and thereafter expressing the DNA in recombinant cell culture.

Substitutional variants are those in which at least one residue has been removed and a different residue inserted in its place. Thus, the polypeptide can also have 1, 2, 3, or 4 substitutions within SEQ ID NO: 1, 2, 3, 4, 5, or 6. Techniques for making substitution mutations at predetermined sites in DNA having a known sequence are well known, for example M13 primer mutagenesis and PCR mutagenesis.

Conservative Substitutions

In certain embodiments, the protein variant has a conservative amino acid substitution in SEQ ID NO: 1, 2, 3, 4, 5, or 6. The replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Mg; and Phe, Tyr.

In contrast, the substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

Percent Identity

It is understood that one way to define the variants and derivatives of the disclosed polypeptides disclosed herein is through defining the variants and derivatives in terms of homology/identity to specific known sequences. Thus, disclosed are variants of these and other disclosed proteins. For example, disclosed are polypeptides having at least, 5, 6, 7, 8, 9, 10, 11, 12, 13, 14, or 15 amino acids in SEQ ID NO: 1, 2, 3, 4, 5, or 6. Thus, disclosed are polypeptides having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 1, 2, 3, 4, 5, or 6.

Those of skill in the art readily understand how to determine the sequence identity of two proteins. For example, the sequence identity can be calculated after aligning the two sequences so that the sequence identity is at its highest level.

Another way of calculating sequence identity can be performed by published algorithms. Optimal alignment of sequences for comparison may be conducted by the local sequence identity algorithm of Smith and Waterman Adv. Appl. Math. 2: 482 (1981), by the sequence identity alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

It is understood that the description of conservative mutations and sequence identity can be combined together in any combination, such as embodiments that have at least 75% sequence identity to a particular sequence wherein the variants are conservative mutations.

Thus, disclosed is an isolated polypeptide having an amino acid sequence that is at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO: 1, 2, 3, 4, 5, or 6 that anti-GD3 antibodies specifically bind to in vivo.

Analogs and Mimetics

It is understood that there are numerous amino acid and peptide analogs which can be incorporated into the disclosed compositions. Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

Thus, also disclosed is a peptidomimetic of the disclosed polypeptides, such as the GD3-like polypeptides that can compete for anti-GD3 antibody binding to GD3. The term "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment can be a peptidomimetic wherein the compound has a bond, a peptide backbone or an amino acid component replaced with a suitable mimic.

Non-Natural Amino Acids

Some non-limiting examples of unnatural amino acids which may be suitable amino acid mimics include β-alanine, L-α-amino butyric acid, L-γ-amino butyric acid, L-α-amino isobutyric acid, L-ϵ-amino caproic acid, 7-amino heptanoic acid, L-aspartic acid, L-glutamic acid, N-ϵ-Boc-N-α-CBZ-L-lysine, N-ϵ-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

There are also numerous D amino acids or amino acids which have a different functional substituent than natural amino acids. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs). D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides.

Modified Amino Acid Linkages

Molecules can be produced that resemble peptides, but which are not connected via a natural peptide linkage. For example, linkages for amino acids or amino acid analogs can include —$CH_2NH$—, —$CH_2S$—, —$CH_2$—$CH_2$—, —CH=CH— (cis and trans), —$COCH_2$—, —CH(OH) $CH_2$—, and —$CHH_2SO$— (these and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications; Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH)$CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Cysteine residues can also be used to cyclize or attach two or more peptides together. This can be beneficial to constrain peptides into particular conformations. (Rizo and Gierasch Ann. Rev. Biochem. 61:387 (1992), incorporated herein by reference).

Synthetic Polypeptide

In some embodiments, the disclosed polypeptides, such as the GD3-like polypeptide, are synthetic. In these embodiments, one or more of the amino acids of the polypeptide are linked together using conventional protein chemistry techniques.

Recombinant Polypeptide

In some embodiments, the disclosed polypeptides, such as the GD3-like polypeptide, are recombinant. In these embodiments, the polypeptide is produced by culturing a cell that expresses a nucleic acid encoding the polypeptide. The nucleic acid can be operably linked to an expression control sequence under conditions suitable for the transcription and translation of the nucleic acid.

Multivalent Peptides

The disclosed polypeptide can be linked together to form divalent or multivalent peptides. In some embodiments, the polypeptides are directly linked together to form a polymer. Thus, disclosed is a polypeptide having two or more polypeptide sequences that compete for the binding of anti-ganglioside antibodies to the ganglioside. Thus, disclosed is a polypeptide having two or more amino acid sequences set forth in SEQ ID NO:1, 2, 3, 4, 5, or 6.

Two or more of the disclosed polypeptide can be linked together to form a conjugate. For example, disclosed is a composition including a first polypeptide having the amino acid sequence SEQ ID NO:1, 2, 3, 4, 5, or 6, or a conservative substitution or deletion thereof, and a second polypeptide having the amino acid sequence SEQ ID NO:1, 2, 3, 4, 5, or 6, or a conservative substitution or deletion thereof, wherein the first and second polypeptides are conjugated together with a linker. The linker can be any molecule, compound, or composition capable of joining two or more polypeptides together. For example, the linker can be one or more amino acids. The linker can be a polymer, such as polyethylene glycol (PEG).

Thus, in some embodiments, the polypeptides are linked to form a dendrimer. Peptide dendrimers are branched, often highly branched, artificial proteins in which several peptide chains branch out from a dendritic core matrix that is built up through the propagation of, for example, a trifunctional amino acid, such as Lys. Originally conceived as Multiple Antigen Presentation System (MAPs) for vaccine development, these molecules are also useful for protein design.

Linkers and Tags

The provided polypeptide can have additional N-terminal, C-terminal, or intermediate amino acid sequences, e.g., amino acid linkers or tags. The term "amino acid linker" refers to an amino acid sequences or insertion that can be used to connect or separate two distinct polypeptides or polypeptide fragments, wherein the linker does not otherwise contribute to the essential function of the composition. The term "amino acid tag" refers to a distinct amino acid sequence that can be used to detect or purify the provided polypeptide, wherein the tag does not otherwise contribute to the essential function of the composition. The provided polypeptide can further have deleted N-terminal, C-terminal or intermediate amino acids that do not contribute to the essential activity of the polypeptide.

Peptide Oral Formulations

Peptides may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. For example, PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane.

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as in the intestine.

To ensure full gastric resistance a coating can be impermeable to at least pH 5.0. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

To aid dissolution of peptides into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of peptides are for instance the fatty acids oleic acid, linoleic acid and linolenic acid.

Controlled release oral formulations may be desirable. The peptides could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The peptides could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Nucleic Acids

Nucleic Acids Encoding the Peptides

Also disclosed are nucleic acids encoding the disclosed polypeptides. Thus, disclosed are all nucleic acids, including degenerate nucleic acids, encoding the disclosed variants and derivatives of the protein sequences. While each particular nucleic acid sequence may not be written out, it is understood that each and every sequence is in fact disclosed and described through the disclosed protein sequence.

The term "nucleic acid" refers to a natural or synthetic molecule having a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

Expression Control Sequences

The nucleic acids that are delivered to cells typically contain expression control systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements. Thus, also disclosed are nucleic acids encoding the disclosed polypeptides operably linked to an expression control sequence.

The term "operably linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative or operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species can also be used.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and contains of about 400 bases. It is also preferred that the transcribed units contain other standard sequences alone or in combination with the above sequences improve expression from, or stability of, the construct.

Vectors Containing the Nucleic Acids

Also disclosed is a vector containing a nucleic acid encoding the disclosed polypeptides. The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors which serve equivalent functions.

In some embodiments the vector is derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens.

Cells Containing Vectors

Also disclosed are cells containing one or more of the disclosed nucleic acids or vectors. The term "cell" refers to individual cells, cell lines, primary culture, or cultures derived from such cells unless specifically indicated. A "culture" refers to a composition having isolated cells of the same or a different type. A cell line is a culture of a particular type of cell that can be reproduced indefinitely, thus making the cell line "immortal." A cell culture can be a population of cells grown on a medium such as agar. A primary cell culture is a culture from a cell or taken directly from a living organism, which is not immortalized.

Additional Moieties

The disclosed compositions can further include additional moieties, such as effector molecules. For example, the disclosed polypeptides, such as the GD3-like polypeptides, can further include an effector molecule.

In some embodiments, the disclosed polypeptide, such as the GD3-like polypeptide, is a chimeric molecule. A "chimeric molecule" is a single molecule created by joining two or more molecules that exist separately in their native state. The single, chimeric molecule has the desired functionality of all of its constituent molecules. Frequently, one of the constituent molecules of a chimeric molecule is a "targeting molecule" or "targeting moiety." The targeting molecule is a molecule such as a ligand or an antibody that specifically binds to its corresponding target, for example a receptor on a cell surface.

In some embodiments, the disclosed polypeptide, such as the GD3-like polypeptide, is a fusion protein having a ganglioside epitope, such as a GD3 epitope. A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

In some embodiments, the disclosed polypeptide, such as the GD3-like polypeptide, that competes for the binding of anti-ganglioside antibodies, such as anti-GD3 antibodies to GD3, is linked to one or more additional moieties by a chemical linkage.

The herein provided compositions can further include an effector molecule. By "effector molecule" is meant a substance that acts upon the target cell(s) or tissue to bring about a desired effect. The effect can, for example, be the labeling, activating, repressing, or killing of the target cell(s) or tissue. Thus, the effector molecule can, for example, be a small molecule, pharmaceutical drug, toxin, fatty acid, detectable marker, conjugating tag, nanoparticle, or enzyme.

Detectable markers include any substance that can be used to label or stain a target tissue or cell(s). Non-limiting examples of detectable markers include radioactive isotopes, enzymes, fluorochromes, and quantum dots (Qdot®). Other known or newly discovered detectable markers are contemplated for use with the provided compositions.

The effector molecule can be covalently linked to the disclosed peptide. The effector molecule can be linked to the amino terminal end of the disclosed peptide. The effector molecule can be linked to the carboxy terminal end of the disclosed peptide. The effector molecule can be linked to an amino acid within the disclosed peptide. The herein provided compositions can further include a linker connecting the effector molecule and disclosed peptide. The disclosed peptide can also be conjugated to a coating molecule such as bovine serum albumin (BSA) (see Tkachenko et al., (2003) J Am Chem Soc, 125, 4700-4701) that can be used to coat the Nanoshells with the peptide.

Protein crosslinkers that can be used to crosslink the effector molecule to the disclosed peptide are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy)ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio)propionamido]butane), BSSS (Bis(sulfosuccinimdyl)suberate), SMPB (Succinimdyl-4-(p-maleimidophenyl)butyrate), SULFO SMPB (Sulfosuccinimdyl-4-(p-maleimidophenyl)butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio)propionamido)hexanoate), SULFO NHS LC SPDP (Sulfosuccinimidyl-6-[3-(2-pyridyldithio)propionamido) hexanoate), SPDP (N-Succinimdyl-3-[(2-pyridyldithio)propionate), NHS BROMOACETATE (N-Hydroxysuccinimidylbromoacetate), NHS IODOACETATE (N-Hydroxysuccinimidyliodoacetate), MPBH (4-(N-Maleimidophenyl)butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS(N-(epsilon-Maleimidocaproyloxy) sulfosuccinimide), EMCS(N-(epsilon-Maleimidocaproyloxy) succinimide), PMPI (N-(p-Maleimidophenyl)isocyanate), KMUH(N-(kappa-Maleimidoundecanoic acid)hydrazide), LC SMCC (Succinimidyl-4-(N-maleimidomethyl)-cyclohexane-1-carboxy(6-amidocaproate)), SULFO GMBS (N-(gamma-Maleimidobutryloxy)sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy)succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

Pharmaceutically Acceptable Carriers
Excipients

The compositions disclosed can be used therapeutically in combination with a pharmaceutically acceptable excipient/carrier. Thus, also disclosed is a pharmaceutical composition having an effective amount of one or more polypeptides disclosed herein and a pharmaceutically acceptable excipient.

The term "therapeutically effective" means that the amount of the composition used is of sufficient quantity to ameliorate one or more causes or symptoms of a disease or disorder, such as neuromuscular weakness in GBS. Such amelioration only requires a reduction or alteration, not necessarily elimination.

By "pharmaceutically acceptable" is meant a material that is not biologically or otherwise undesirable, i.e., the material may be administered to a subject, along with the disclosed polypeptide, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical excipients are known to those skilled in the art. These most typically would be standard carriers for administration of drugs to humans, including solutions such as sterile water, saline, and buffered solutions at physiological pH. Pharmaceutical compositions may include carriers, thickeners, diluents, buffers, preservatives, surface active agents and the like in addition to the active agent. Pharmaceutical compositions may also include one or more active ingredients such as antimicrobial agents, anti-inflammatory agents, anesthetics, and the like.

Suitable pharmaceutical preparations include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Suitable formulations include sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amities and substituted ethanolamines.

Liposomes

Also disclosed is a pharmaceutical composition having an effective amount of one or more polypeptides disclosed in a liposome. The term "liposome" refers to a structure having an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 μm. These MLVs were first described by Bangham, et al., J. Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamnellar vesicles, which are prepared by more extensive sonication of MLVs, and are made of a single spherical lipid bilayer surrounding an aqueous solution. Unilamellar vesicles ("ULVs") can be small, having diameters within the range of 20 to 200 nm, while larger ULVs can have diameters within the range of 200 nm to 2 μm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 μm, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

Fatty acids (i.e., lipids) that can be conjugated to the provided compositions include those that allow the efficient incorporation of the disclosed compositions into liposomes. Generally, the fatty acid is a polar lipid. Thus, the fatty acid can be a phospholipid. The provided compositions can include either natural or synthetic phospholipid. The phospholipids can be selected from phospholipids containing saturated or unsaturated mono or disubstituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmitielinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidlcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Albaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)- oleoyl (18:1)-PC, and myristoyl (14:0)-oleoyl (18:1)-PC as constituents. Thus, as an example, the provided compositions can include palmitoyl 16:0.

Animal Model of Guillain-Barré Syndrome

Also disclosed is an animal model of Guillain-Barré syndrome (GBS). The animal model can be a non-human animal inoculated with $LOS_{GD3}$. Thus, the animal model can be a non-human animal inoculated with a lipooligosaccharide having the saccharide sequence NeuAc-NeuAc-Gal-Hep.

In some embodiments, the non-human animal has circulating antibodies that specifically bind the GD3 ganglioside NeuAcα2-8NeuAcα2-3Galβ1-4Glcβ1-1'Cer.

The disclosed animals can be any non-human animal, including a non-human mammal (e.g., mouse, rat, rabbit, squirrel, hamster, rabbits, guinea pigs, pigs, micro-pigs, prairie dogs, baboons, squirrel monkeys and chimpanzees, etc), bird or an amphibian. For example, the animal can be avian, bovine, canine, caprine, equine, feline, leporine, murine, ovine, porcine, or non-human primate. Thus, the animal can be a rodent or lagomorph. Thus, the animal can be a mouse, a rabbit, or a rat.

Suitable animals can be obtained from standard commercial sources such as Charles River (Wilmington, Mass.), Taconic (Germantown, N.Y.), and Harlan Sprague Dawley (Indianapolis, Ind.).

Screening Methods

Identifying Ganglioside-Epitopes

Also provided is a method of identifying an agent that can be used to treat GBS. In some embodiments, the method involves identifying molecules, such as polypeptides, having a ganglioside epitope, such as a GD3 epitope.

The method can involve providing a sample having anti-ganglioside antibodies, such as anti-GD3 antibodies, under conditions that allow the binding of anti-ganglioside antibody to the ganglioside, contacting the sample with a candidate molecule, detecting the level of antibody/ganglioside binding, comparing the binding level to a control, a decrease in antibody/ganglioside binding compared to the control identifying a molecule that can be used to treat GBS.

The method can alternatively involve providing a sample having anti-ganglioside antibodies, such as anti-GD3 antibodies, under physiological conditions, contacting the sample with a candidate molecule, and detecting the ability of the antibody to specifically bind to the candidate molecule, wherein the ability of the antibodies to specifically bind the candidate molecule being is an indication that the molecule can be used to treat GBS.

The binding of the antibody to the ganglioside or the candidate molecule can be detected using routine methods, such as immunodetection methods, that do not disturb protein binding. The methods can be cell-based or cell-free assays. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon. Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods. In addition, those skilled in the art of drug discovery and development readily understand that methods for dereplication (e.g., taxonomic dereplication, biological dereplication, and chemical dereplication, or any combination thereof).

When a crude extract is found to have a desired activity, further fractionation of the positive lead extract is necessary to isolate chemical constituents responsible for the observed effect. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions, such as those disclosed herein.

Candidate agents encompass numerous chemical classes, but are most often organic molecules, e.g., small organic compounds having a molecular weight of more than 100 and less than about 2,500 daltons. Candidate agents include functional groups necessary for structural interaction with proteins, particularly hydrogen bonding, and typically include at least an amine, carbonyl, hydroxyl or carboxyl group, for example, at least two of the functional chemical groups. The candidate agents often have cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In a further embodiment, candidate agents are peptides.

In some embodiments, the candidate agents are proteins. In some aspects, the candidate agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and vertebrate proteins, and human proteins.

Methods of Making the Compositions

The compositions disclosed herein and the compositions necessary to perform the disclosed methods can be made using any method known to those of skill in the art for that particular reagent or compound unless otherwise specifically noted.

Peptide Synthesis

For example, one method of producing the disclosed proteins, such as SEQ ID NOs:1-6, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method is a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Nucleic Acid Synthesis

Likewise, the nucleic acids can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

EXAMPLES

Example 1

Purification of $LOS_{GD3}$ from the LOS Fraction of C. Jejuni

Materials and Methods

Preparation of R24 mAb

The hybridoma cell line for mAb R24 (IgG3) was cultivated in serum-free cell cultures (BD Cell MAb Medium Serum Free; Becton Dickinson and Company, Sparks, Md.). A small aliquot of the supernatant from routine cell culture was tested for IgG production using the IsoStrip Monoclonal Antibody Isotyping Kit (Santa Cruz Biotechnology, Santa Cruz, Calif.). Each of the collected conditioned media was concentrated about 20-fold using an Amicon concentrator (model No. 8200) with an ultrafiltration membrane YM10 (Millipore Corp., Bedford, Mass.). After concentration, the IgG fraction of mAb R24 was precipitated with a saturated solution of ammonium sulfate (80 g dissolved in 100 ml of hot water) and dialyzed against phosphate-buffered saline (PBS) in water for 4 days at 4° C., and the dialyzed IgG proteins were further purified by affinity column chromatography (HiTrap Protein G HP, 1 ml; Amersham Bioscience, Uppsala, Sweden). The IgG fraction was recovered from the column by eluting with a glycine buffer (0.1 M glycine-HCl, pH 2.7); the eluting solution was neutralized by addition of 1 M NaOH and then dialyzed against PBS for 3 days at 4° C. Finally, the dialyzed mAb R24-IgG protein was used for ELISA and constructing the mAb R24 affinity column.

Preparation of $LOS_{GD3}$

C. jejuni ATCC-43446 (serotype HS:19) was grown in Brucella broth with gentle shaking (100-150 rpm) for 48 hr at 37° C. under microaerobic conditions. The cells were recovered by centrifugation at 4,000 rpm for 30 min and washed twice with saline. The LOS fraction was extracted from the cell pellets by the hot phenol-water procedure (Westphal et al., 1952. Z Naturforsch 7b: 148-155), and isolation of LOS$_{GD3}$ was done as described previously (Usuki et al., 2006. *J Neurosci Res* 83: 274-284). The protocol outline is shown in FIG. 1. Treatment of the cell pellets of *C. jejuni* with a hot phenol solution yielded aqueous and phenolic phases. The aqueous phase was dialyzed against water and the dialysate treated with 2 vol of methanol and 1 vol of chloroform. The chloroform layer was recovered by a separatory funnel, and the aqueous layer was again partitioned with 1 vol of chloroform and 1 vol of water. The chloroform layer was recovered and combined with the previous chloroform layer. Most of the LOS was recovered in the combined chloroform fraction. An additional minor amount of LOS was precipitated at 4° C. overnight from the remaining phenolic phase by the addition of 9 vol of cold acetone. The two LOS fractions thus obtained were combined, dried, and subjected to alkaline hydrolysis with 25% ammonia at 56° C. for 48 hr. The solution was then dialyzed against water, and the retentate was lyophilized.

FIG. 1 shows the isolation scheme for LOS$_{GD3}$ from crude LOS fraction. The steps involved in the isolation and purification of LOS$_{GD3}$ are shown. LS, a major LOS component characterized as a slow-migrating band based on the TLC of CTxb overlay; LF, a minor LOS component characterized as a fast-migrating band based on the TLC of CTxb overlay. Fractions 1-4: Stepwise elution from a silica gel column with the following solvents: 1) n-propanol, 2) n-propanol:H$_2$O (75:20 v/v), 3) n-propanol: H$_2$O:triethylamine (75:20:5 v/v/v), and 4) n-propanol: H$_2$O:triethylamine (60:20:20 v/v/v). Fractions 5-8: Stepwise eluting from an mAb R24 affinity column with the following solvents: 5) washing solution 1 (10 mol of 1 and 10 mM PBS), 6) washing solution 2 (50 mM PBS), 7) eluting solution 1 (5 ml of 50 mM diethylamine/HCl buffer, pH 8.6, containing 0.1 M NaCl), and 8) eluting solution 2 (5 ml of 50 mM diethylamine/HCl buffer, pH 10.5, containing 0.1 M NaCl).

The LOS fraction described above was further fractionated by stepwise elution from a silica gel column (13×1.5 cm i.d.; Iatrobeads 6RS-8060; Iatron Laboratories, Tokyo, Japan) using the following solvents in succession: 1) 60 ml n-propanol, 2) 40 ml n-propanol:H$_2$O (75:20, v/v), 3) 100 ml n-propanol:H$_2$O:triethylamine (75:20:5, v/v/v), and 4) 100 ml n-propanol:H$_2$O:triethylamine (60:20:20, v/v/v). The fraction eluted with solvent 3 was collected, and the aliquot was tested by two separate TLC-immune overlays to detect LOS$_{GD3}$ and LOS$_{GM1}$. A portion of the sample was developed on an HPTLC plate using the solvent system of n-propanol: H$_2$O:25% NH3 (6:3:1, v/v/v). After the plate was dried, the plate was overlaid with anti-GD3 mAb R24 (1:5 dilution). Another similarly developed plate was overlaid with cholera toxin B subunit (CTxb) as described previously (Usuki et al., 2006b. *J Neurosci Res* 83: 274-284; Usuki et al., 2007. *Glycoconj J* 24: 167-180).

For affinity purification, the purified R24 IgG protein mentioned above was dialyzed in coupling buffer (0.1 M NaHCO$_3$, pH 8.0) and coupled with affinity gel CNBr-sepharose 4B (Sigma, St. Louis, Mo.) using a previously described procedure. The column was preeluted with 3 M potassium thiocyanate in 0.5 M ammonium hydroxide and washed well with 1 mM PBS. The LOS fraction eluted with solvents 3 and 4 from the silica gel column was applied onto an affinity column (column volume 1 ml) and eluted stepwise with the following solvents (FIG. 1): 5) washing solution 1 (10 ml of 1 and 10 mM PBS); 6) washing solution 2 (50 mM PBS); 7) eluting solution 1 (5 ml of 50 mM diethylamine/HCl buffer, pH 8.6, containing 0.1 M NaCl); and 8) eluting solution 2 (5 ml of 50 mM diethylamine/HCl buffer, pH 10.5, containing 0.1 M NaCl). The bound LOS fraction was eluted with solvents 7 and 8, consecutively, of the affinity column and recovered in 0.5-ml fractions. R24-binding LOS (LOS$_{GD3}$) was present in the 10th to 15th tubes of the eluting solutions. These fractions were collected, combined, dialyzed against water, and lyophilized as LOS$_{GD3}$. LOS$_{GD3}$ was stored at −20° C. before use.

Results

LOS$_{GD3}$ was purified from a cell pellet of *C. jejuni*, strain HS19 (30.5 g wet weight) according to the procedure outlined in FIG. 1. After silica gel column chromatography, a total of 1.72 g of the LS fraction was recovered in fractions 3 and 4. The crude LS fractions were combined and further fractionated by an mAb R24 affinity column. Each of the column fractions from the silica gel and the mAb R24 affinity chromatography was examined by TLC-immuno-overlay with mAb R24 and CTxb. LOS$_{GD3}$ was associated with LOS$_{GM1}$. mAb R24 affinity chromatography successfully allowed elution of LOS$_{GD3}$ into fractions 7 and 8 and separation of LOS$_{GD3}$ from LOS$_{GM1}$. Finally, 140 mg LOS$_{GD3}$ was purified and used for further experiments.

Example 2

Competitive Inhibition Assay

Materials and Methods
Preparation of BEC2 mAb

The hybridoma cell line for mAb BEC2 (IgG2b) was cultivated in serum-free cell cultures (BD Cell MAb Medium Serum Free; Becton Dickinson and Company, Sparks, Md.). A small aliquot of the supernatant from routine cell culture was tested for IgG production using the IsoStrip Monoclonal Antibody Isotyping Kit (Santa Cruz Biotechnology, Santa Cruz, Calif.). Each of the collected conditioned media was concentrated about 20-fold using an Amicon concentrator (model No. 8200) with an ultrafiltration membrane YM10 (Millipore Corp., Bedford, Mass.). After concentration, the IgG fraction of BEC2 was precipitated with a saturated solution of ammonium sulfate (80 g dissolved in 100 ml of hot water) and dialyzed against phosphate-buffered saline (PBS) in water for 4 days at 4° C., and the dialyzed IgG proteins were further purified by affinity column chromatography (HiTrap Protein G HP, 1 ml; Amersham Bioscience, Uppsala, Sweden). The IgG fraction was recovered from the column by eluting with a glycine buffer (0.1 M glycine-HCl, pH 2.7); the eluting solution was neutralized by addition of 1 M NaOH and then dialyzed against PBS for 3 days at 4° C. Finally, the dialyzed BEC2 IgG protein was biotinylated (see below), and the biotinylated BEC2 (bBEC2) was used for ELISA.

Streptavidin-Coated ELISA for bBEC2 bBEC2 was attached onto streptavidin-coated 96-well polystryrene plates, obtained from Pierce (Rockford, Ill.; No. 15121), and ELISA was performed according to the manufacturer's instructions. The efficacy of binding of the anti-GD3 antibody to immobilized bBEC2 was determined by using mAb R24, followed by an anti-mouse horseradish peroxidase-conjugated secondary antibody and calorimetric development. Briefly, the plasma samples from single-dose administration of bBEC2 were applied to the streptavidin-coated ELISA plate at serial double dilutions in 1% BSA/PBS solution. The plate was subjected to incubation for 1 hr at room temperature, and, after washing with 1% BSA/PBS buffer, each well of the plate was treated with the mAb R24 (1 μg/ml in 1% BSA/PBS). After washing with 1% BSA/PBS buffer, each well was treated with an anti-mouse IgG horseradish peroxidase-conjugated antibody (Jackson Immoresearch, West Grove, Pa.). This secondary antibody was pretreated with rat IgG to eliminate contamination from any anti-rat IgG binding activity. Finally, the bound secondary antibody was visualized by a color-generating reagent (OPD Peroxidase Substrate in PBS; Sigma). Half-saturation absorbance values for plasma samples were estimated by serial plasma dilution curves of ELISA. The absorbances were then converted into values of plasma concentration using a standard serial dilution curve of rat serum containing an authentic bBEC2 sample.

Results

Figure 3A:
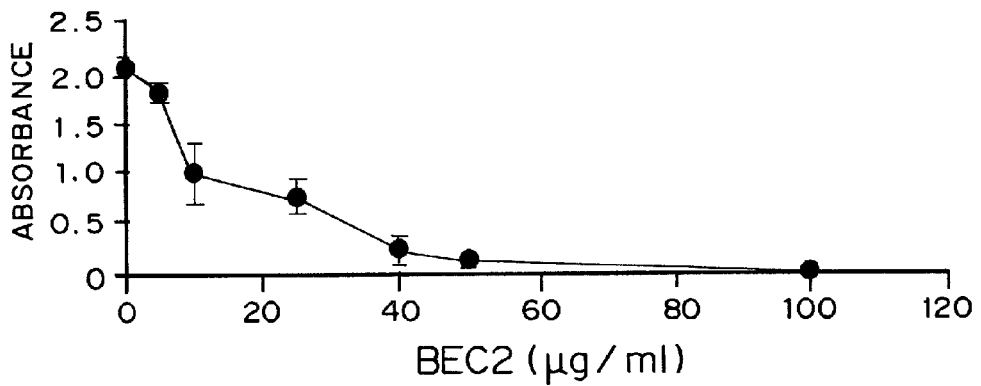
FIG. 3A is a graph showing absorbance in an ELISA plate coated with 0.1 µg GD3 as a function of the concentration of the BEC2 (µg/ml) incubated with MAb R24 prior to addition to the ELISA wells.
Figure 3B:
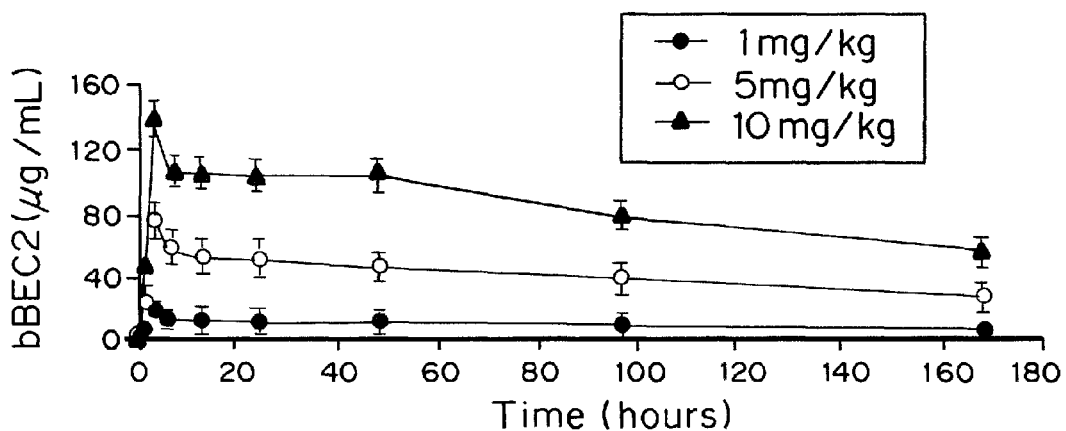
FIG. 3B is a graph showing the mean plasma concentration of BEC2 (µg/ml) in rats as a function of time (h) following i.p. single dosing with 1 mg/kg (closed circle), 5 mg/kg (open circle), or 10 mg/kg (triangle) bBEC2.
Figure 3C:
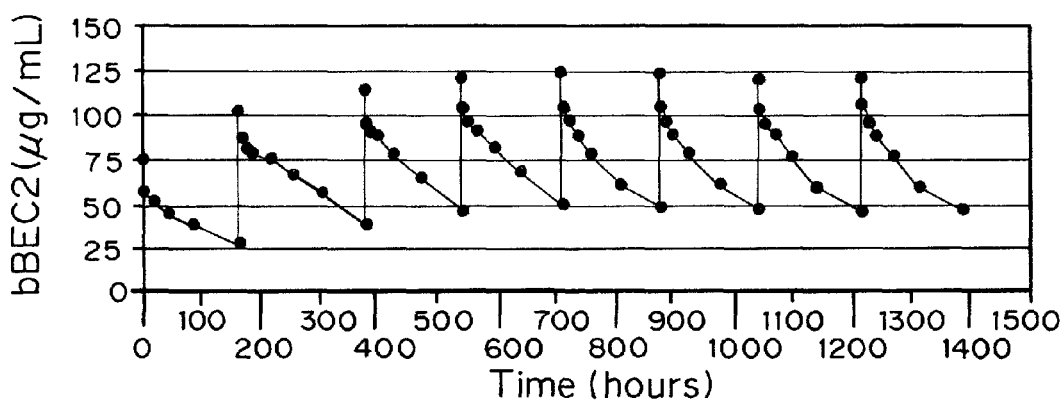
FIG. 3C is a graph simulating concentration of BEC2 (µg/ml) as a function of time (h) following dosing with 5 mg/kg bBEC2 once per week for 8 weeks.
Figure 4A:
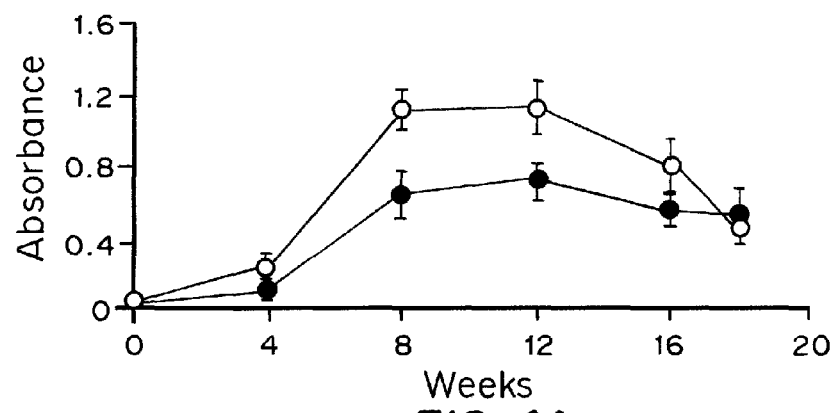
FIGS. 4A-4D are graphs showing serum levels (ELISA absorbance) of anti-GD3 antibody (solid circles) and anti-$LOS_{GD3}$ antibody (open circles) in rats as a function of time (weeks) after administration of $LOS_{GD3}$ (FIG. 4A), Vehicle (FIG. 4B), $LOS_{GD3}$/BEC2 (FIG. 4C), and Vehicle/BEC2 (FIG. 4D).
Figure 4B:
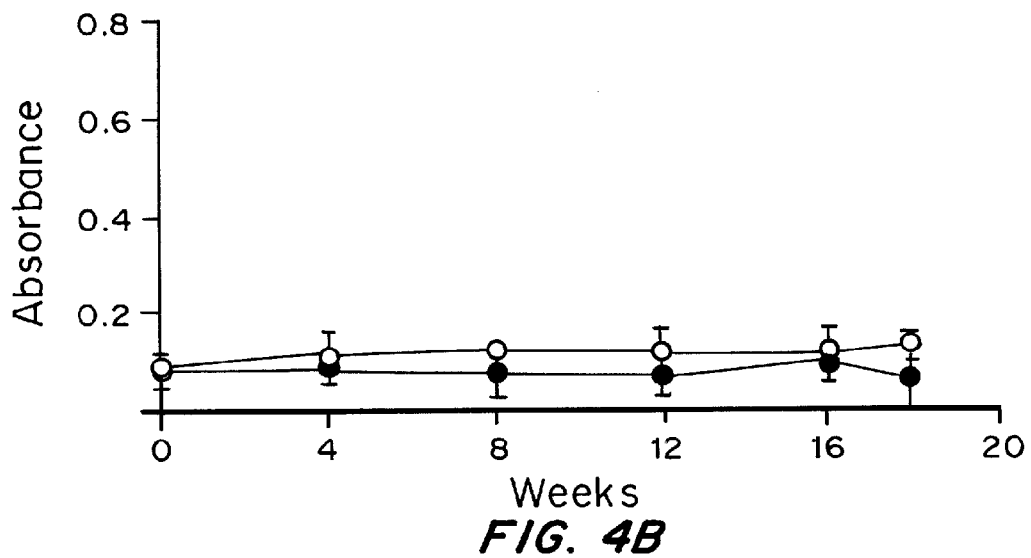
Figure 4C:
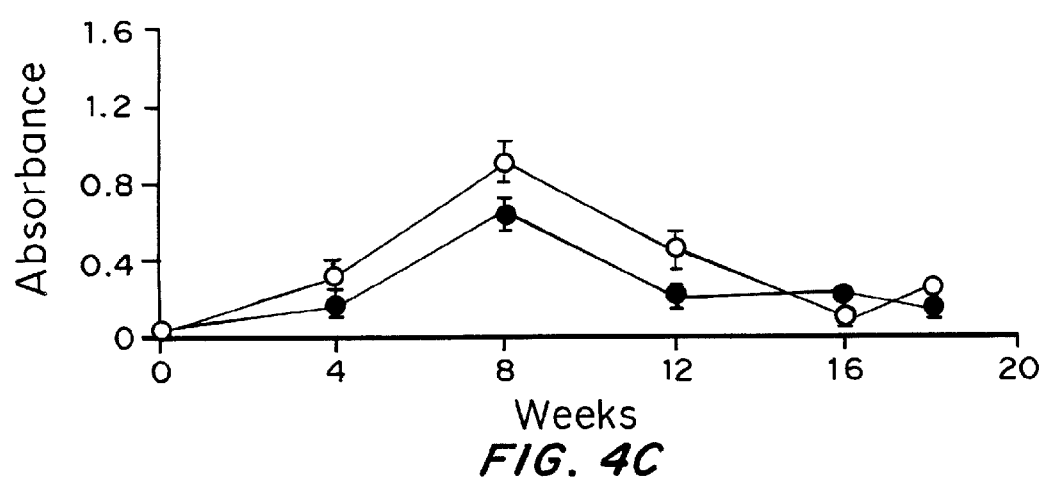
Figure 4D:
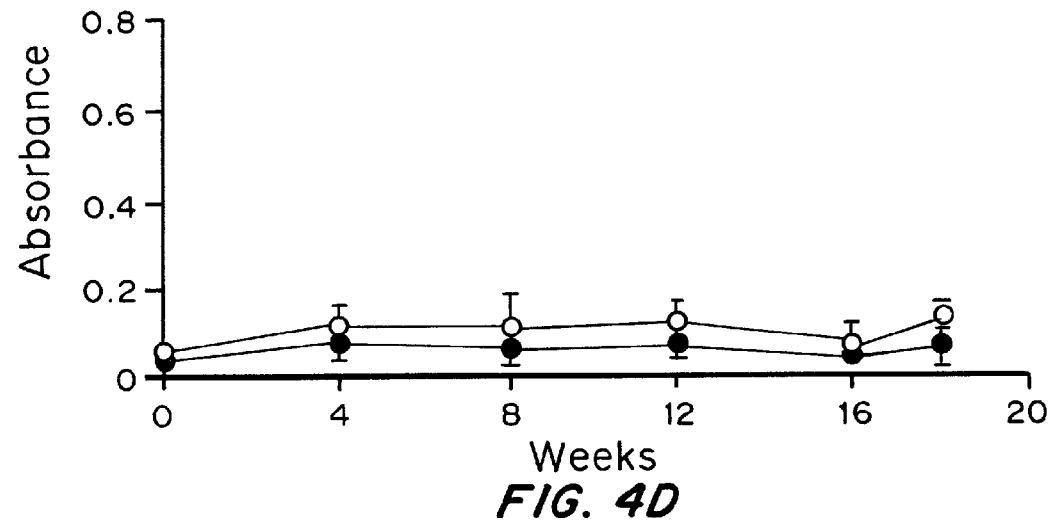

BEC2 was tested for competitive inhibition by ELISA. BEC2 was inhibitory at an $IC_{50}$ of 10 µg/ml, and there was full inhibition at 60 µg/ml (FIG. 3A). FIG. 3 shows dose-dependent inhibition of binding of mAb R24 to GD3 by BEC2. As shown in FIG. 3A, BEC2 was first incubated with MAb R24 at room temperature for 30 min at various concentrations as indicated on the horizontal axis. Subsequently, an aliquot (100 µl) was added to each well, and each well of the ELISA plate was coated with 0.1 µg GD3. The remaining binding activity of mAb R24 was determined by ELISA. Values are means±SD, n=6 individual experiments. As shown in FIG. 3B, mean plasma concentration-time profiles following i.p. single dosing with 1 mg $kg^{-1}$, 5 mg $kg^{-1}$, or 10 mg $kg^{-1}$ bBEC2. The experiment at each dose was performed on three rats, and values are means±SD. As shown in FIG. 3C, simulation of concentration-time course of 5 mg $kg^{-1}$ bBEC2 once per week for 8 weeks. The simulation was performed with values of $t_{1/2}\beta$ and AUC for 5 mg $kg^{-1}$ bBEC2, as shown in Table I.

Example 3

Pharmacokinetic Study

Materials and Methods
Biotinylation of BEC2

The BEC2-IgG protein was biotinylated by using an EZ-Link Sulfa-NHS-LC-Biotinylation Kit (Pierce, Rockford, Ill.). One to ten milligrams BEC2-IgG was dissolved in 0.5-2 ml PBS according to the instruction kit. After addition of the Sulfa-NHS-LC-Biotin solution, the reaction mixture was incubated at room temperature for 1 hr, and the biotinylated product was purified by a Zeba Desalt Spin Column. Estimation of biotin incorporation to BEC2-IgG was done using HABA (4'-hydroxyazobenzene-2-carboxylic acid) Biotin Quantitation Kit (Pierce, Rockford, Ill.) and expressed as mmole biotin/mmole protein.

Pharmacokinetic Analysis

Each female rat was given a single dose of bBEC2 (1, 5, or 10 mg $kg^{-1}$; n=3 per group). The total number (n) was 9 (body weight=200±20 g). Serial blood samples (~200 µl) were taken from tail vein for bBEC2 for predose (0 hr) and from the tail vein at serial time points (1, 3, 6, 12, 24, 48, 96, and 168 hr) postdose. Blood was centrifuged at room temperature, plasma harvested, and stored at −60° C. to −80° C. until analyzed by a streptavidin-coated ELISA plate assay for total concentration of bBEC2.

The plasma concentration-time data of bBEC2 were analyzed by a noncompartmental method of i.p. administration with first-order output as previously reported (Wahl et al., 1988. *Cancer Immunol Immunother* 26: 187-201; Barrett et al., 1997. *Cancer Immunol Immunother* 44: 173-178). The following parameters were calculated: maximum observed plasma concentration ($C_{max}$), area under the plasma concentration-time curve from zero to infinite time point (AUC), plasma clearance (CL), distribution half-life ($t_{1/2}\alpha$), and elimination half-life ($t_{1/2}\beta$). Calculations of rate constants $t_{1/2}\alpha$ and $t_{1/2}\beta$ were obtained by the curve-peeling method (Gibaldi and Perrier, 1982. Pharmacokinetics, 2nd ed. New York: Marcel Dekker). AUC was estimated according to the method of the trapezoidal rule by including the remaining AUC after the last measurable time point (168 hr), extrapolating the curve from the last time point to infinity.

Results

Dosage schedule of BEC2 for animal experiments was designed by pharmacokinetic analysis based on a single dose to the animal. BEC2 was successfully biotinylated. The specific activity for biotin labeling was determined as 0.9 for bBEC2 (mole of biotin per mole of protein).

The purified bBEC2 was administered via i.p. to animals. The plasma concentration vs. time data resulting from single doses of 1, 5, and 10 mg $kg^{-1}$ for BEC2 are plotted in FIG. 3B. None of the experimental rats died or experienced any observable toxicity as a result of the drug administration.

Table 1 lists the parameter values obtained from a non-compartmental analysis of bBEC2. The concentration vs. time data showed a two-phase attenuation of distribution and elimination expressed as $t_{1/2}\alpha$ and $t_{1/2}\beta$. There was no change in parameter values for clearance, $t_{1/2}\alpha$, or $t_{1/2}\beta$ in the single-dose range of 1.0-10.0 mg $kg^{-1}$ for bBEC2. According to linearity parameters, bBEC2 exhibits linear pharmacokinetics after multiple doses. In consideration of $t_{1/2}\beta$ and minimum effective plasma concentrations from a single-dose data point, we adopted chronic i.p. administration of 5 mg $kg^{-1}$ bBEC2 (FIG. 3B). The dosing simulation was processed by multiple (5 mg $kg^{-1}$ once weekly for 8 weeks) i.p. dose administration of bBEC2 (FIG. 3C). The results derived from the multiple-dosing simulation suggested that average and minimum concentrations were 87 µg/ml and 50 µg/ml of BEC2, respectively.

TABLE 1

Pharmacokinetic Parameters After i.p. Administration of BEC2 to Normal Lewis Rats

| Parameter | | bBEC2 dose group | | |
|---|---|---|---|---|
| | | n = 3 | n = 3 | n = 3 |
| Dose | (mg $kg^{-1}$) | 1.0 | 5.0 | 10.0 |
| tmax | (hr) | 3.0 | 3.0 | 3.0 |
| Cmax | (µg $ml^{-1}$) | 15.5 (0.53) | 74.7 (4.7) | 141.4 (9.5) |
| t½α | (hr) | 7.3 (1.4) | 7.1 (1.0) | 7.5 (0.2) |
| t½β | (hr) | 169.3 (8.3) | 161.3 (6.4) | 167.8 (6.1) |
| CL | (ml $hr^{-1}$) | 0.37 (0.06) | 0.47 (0.06) | 0.46 (0.04) |
| Vdss | (ml) | ND | ND | ND |
| AUC | (µg $ml^{-1}$ hr) | 2,757 (434) | 10,750 (1,329) | 22,940 (2,041) |

The values are the means ± (SD).
ND, not determined.
Vdss, steady-state volume of distribution.

Before administration, the BEC2 was subjected to purification by passing through an endotoxin removal column. The final endotoxin level was below 0.1 EU/ml after three or four repeated endotoxin-removal processes.

Example 4

Experimental Animals

Materials and Methods
Animal Experimental Protocol

Figure 2:
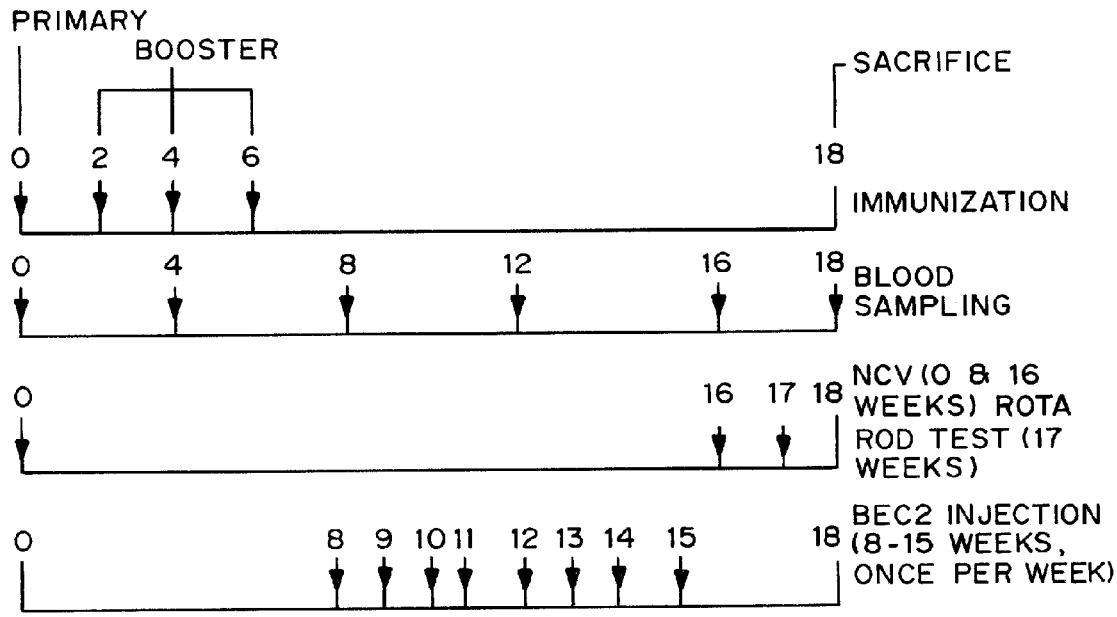
FIG. 2 is a diagram showing the experimental schedule for animal treatments with $LOS_{GD3}$.

Immunization was performed according to a previously described procedure (Usuki et al., 2006. *J Neurosci Res* 83: 274-284) and is shown in FIG. 2. Twelve-week-old female Lewis rats weighing 200-250 g were used. One hundred micrograms $LOS_{GD3}$ was dissolved in 50 mM PBS buffer with a vehicle of 0.05 ml keyhole limpet hemocyanin (KLH; 2 mg/ml) and emulsified with an equal volume of complete Freund's adjuvant (CFA). Rats were given a single subcutaneous injection of 0.1 ml inoculum (or vehicle) into the shoulders and the footpads of the hind limbs. In addition, booster injections were administered similarly to injections in $LOS_{GD3}$ (or vehicle)-treated animals at 2-week intervals with 100 µg $LOS_{GD3}$ (or no additive) and 2 mg/ml KLH in PBS emulsified with an equal volume of incomplete Freund's adjuvant (ICFA) 6 weeks thereafter. Sixteen experimental animals were divided into four groups (n 4 each): 1) $LOS_{GD3}$, 2) $LOS_{GD3}$/BEC2, 3) vehicle, and 4) vehicle/BEC2. The remaining animals were included as the untreated control group (n=4). As shown in the third and fourth stepladders of FIG. 2, BEC2 (5 mg kg$^{-1}$) was administered to rats once per week from 8 to 15 weeks.

FIG. 2 shows experimental schedule of animal treatments. The timing of treatment and performance is shown between 0 and 18 weeks in the experimental period. Sixteen experimental animals were divided into three inoculum-treated groups (n=4, each): 1) $LOS_{GD3}$, 2) $LOS_{GD3}$/BEC2, 3) vehicle, and 4) vehicle/BEC2. The remaining four animals were included as the untreated control group (n 4).

Before injection of BEC2 to the animals, any endotoxin included in the BEC2 was removed by ToxinEraser Endotoxin Removal Kit (GenScript Corp., Piscataway, N.J.), and the endotoxin remaining after the passages was detected by the *Limulus* amebocyte lysate (LAL) test (ToxinSensor™ Gel Clot Endotoxin Assay Kit; GenScript Corp.).

The blood samples were drawn retroorbitally by bleeding with a capillary tube at 0, 4, 8, 12, 16, and 18 weeks after the primary immunization. All experimental animals were weighed and assessed for clinical signs of peripheral nerve abnormalities. Electrophysiological measurements of the rats' nerve conduction velocity (NCV) were made at 0 and 16 weeks, with a rotarod test at 17 weeks after the primary immunization. All animals were allowed free access to water and food. The use of these animals had been approved by the Medical College of Georgia's Institutional Animal Care and Use Committee. Treatment of these animals was performed according to approved procedures.

Results

Consistent with previous findings with crude LOS (Usuki et al., 2006. *J Neurosci Res* 83: 274-284), the $LOS_{GD3}$ treatment showed mild clinical signs of neurological dysfunctions, including a remarkable slowness of motion and noticeable weight loss during 13-18 weeks compared with vehicle treatment. Despite a significant lowering of NCVs, the $LOS_{GD3}$-treated rats did not show any flaccid limb paralysis or standing still during the same period. However, they were judged as having mild nerve dysfunctions from their rotarod performance. Furthermore, nerve dysfunctions were substantiated by pathological examination with loss of myelin in myelinated fibers. At the endpoint of the experiment, all animals were sacrificed and dissected. There was no evidence of adhesive peritonitis or abdominal dropsy resulting from infection in animals with administration by multiple i.p. doses of BEC2.

Example 5

Time Course of Anti-GD3 and Anti-$LOS_{GD3}$ Antibody Production

Materials and Methods
ELISA for Gangliosides and $LOS_{GD3}$
Antiganglioside antibody activity was evaluated for GM1, GM2, GD1a, GD1b, GT1b, GQ1b, GD3, and $LOS_{GD3}$ by conventional ELISA method (Usuki et al., 2005. *J Neurol Sci* 232: 37-44). To measure half-maximal inhibitory concentrations (IC$_{50}$s) of BEC2 against mAb R24 binding to GD3, each well of the ELISA plate (Immunlon 1B; Lab System, Franklin, Mass.) was coated with 0.1 µg GD3. Before the ELISA plate assay, each well was treated with 1% BSA/PBS solution. The purified mAb R24 IgG (10 µg/ml by 1% BSA/PBS solution) was incubated with various concentrations of BEC2 for 30 min. After incubation, the reaction mixture was passed through a 0.22-µm syringe filter (Millipore Corp., Bedford, Mass.). Subsequently, 100 µl of the mixture was added to each well and incubated for 1 hr at room temperature. To each of the wells, a secondary antibody (horseradish peroxidase-conjugated anti-mouse IgG, 1:5,000 dilution in 1% BSA/PBS solution) was added and incubated for 1 hr at room temperature. Finally, the bound secondary antibody was visualized by addition of a color-generating reagent (OPD Peroxidase Substrate). The absorbance was measured at 492 nm with a microplate spectrophotometer (Bio-Rad, Hemel Hempstead, United Kingdom). The nomenclature of gangliosides is based on that of Svennerholm (Svennerholm, 1964. *J Lipid Res* 5: 145-155).

Results

Anti-GD3 and anti-$LOS_{GD3}$ antibody responses for sensitization by $LOS_{GD3}$ were examined chronically by testing for ELISA absorbance of rat serum samples (FIG. 4). Antibodies for GM1, GM2, GD1a, GD1b, GT1b, and GQ1b were not detected in these sera during the entire course of the animal experiment (data not shown). The anti-GD3 IgG antibody titer was elevated 8 weeks postinoculation, in parallel with elevation of the anti-$LOS_{GD3}$ antibody titer. The anti-GD3 IgG antibody titer was maintained at a plateau during 8-12 weeks and decreased slightly after 12-16 weeks (FIG. 4A). The titer of serum anti-GD3 antibody was elevated (8-12 weeks; FIG. 4A), and this period was involved with BEC2 treatment, which extended to 15 weeks (FIG. 2, bottom stepladder). There were no IgG antibody responses for GD3 in the vehicle-treated group or the untreated group (FIG. 4B). The $LOS_{GD3}$/BEC2 group showed a remarkable suppression of anti-$LOS_{GD3}$ and anti-GD3 antibodies after chronic treatment with BEC2 (FIG. 4C), whereas vehicle/BEC2 treatment was ineffective (FIG. 4D).

FIGS. 4A-5D show changes of serum level of the anti-GD3 antibody and the anti-$LOS_{GD3}$ antibody of rats. According to the experimental schedule shown in FIG. 2, animal serum samples were obtained at the specified times to test activities of anti-GD3 antibody (solid circles) and anti-LOS GD3 antibody (open circles) using ELISA. Values are means±SD for four animals.

Example 6

NCV Changes

Materials and Methods
NCVs
NCVs (m/sec) were measured in the rat tail nerve using a Nicolet VikingQuest EMG machine (NeuroCare Group, Madison, Wis.) according to the modified procedure of Andersen et al. (1994. *Muscle Nerve* 17: 80-84). In brief, the nerves were stimulated using external digital ring electrodes with twisted wires (Medtronic Functional Diagnostics, Skovlunde, Denmark) instead of needle electrodes (Usuki et al., 2006. *J Neurosci Res* 83: 274-284). The electrodes were placed in segments proximal (5 cm) and distal (2 cm) to the recording position (7 cm from the rat tail joint). NCV was evaluated from four different waves generated from electrical stimulations; each wave showed a reproducible pattern and also showed the same amplitude level as the stimulator voltage was increased. During measurement, a constant surface temperature of the rat tail was maintained at 34-35° C. Each NCV value represents an average value of four nerve conduction wave measurements per animal.

Statistical Analysis

Statistical analyses were performed in the GraphPad Prism 2.01 software package (GraphPad, San Diego, Calif.). One-way ANOVA was performed for data from the experimental animal groups, followed by Tukey's multiple-comparisons test. Differences in the control group vs. the $LOS_{GD3}$-treated group were analyzed by Dunnett's multiple-comparisons test.

Results

Figure 5A:
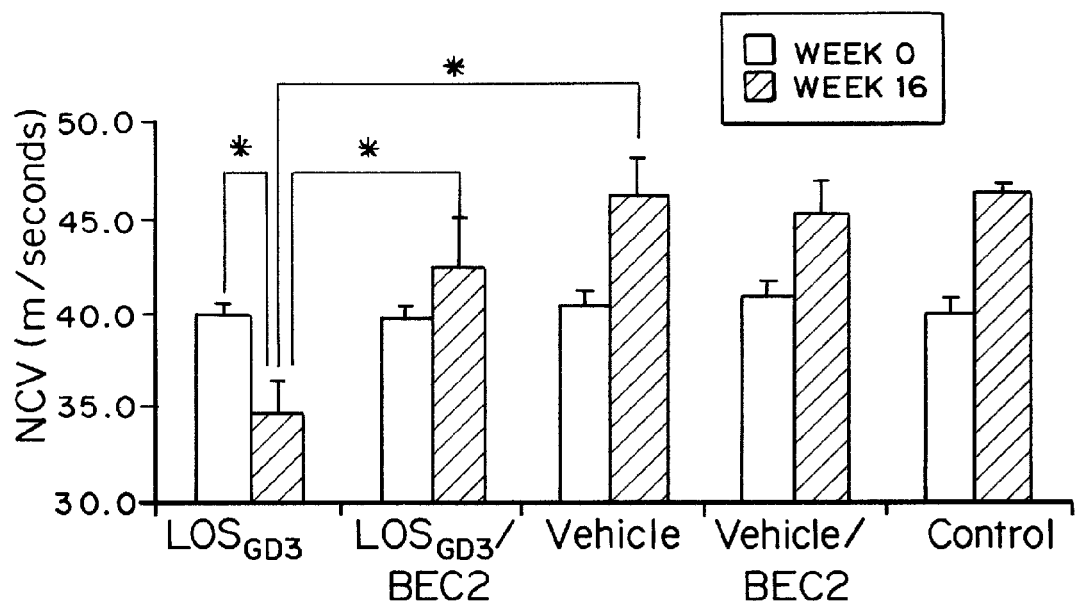
FIG. 5A is a bar graph showing nerve conduction velocity (NCV) (m/sec) at week 0 (open bars) and week 16 (closed bars) after primary immunization by $LOS_{GD3}$ (first set of bars), $LOS_{GD3}$/BEC2 (second set of bars), Vehicle (third set of bars), Vehicle/BEC2 (fourth set of bars), and Control (fifth set of bars).

NCVs were measured at the beginning and the endpoint according to the experimental schedule of treatments. As shown in FIG. 5A, according to the treatment schedule, control rats showed increased NCV within the experimental period, presumably resulting from an age-related change (Birren and Wall, 1956. *J Comp Neural* 104: 1-16). At 16 weeks, the NCV of the group sensitized by $LOS_{GD3}$ decreased significantly compared with the vehicle group (P<0.01). BEC2 showed improved relative attenuation of NCV, and a statistically significant difference was observed between $LOS_{GD3}$ and $LOS_{GD3}$/BEC2. No effect on NCV, other than the age-dependent change, was observed for animals treated with vehicle or BEC2 alone (FIG. 5A).

Figure 5B:
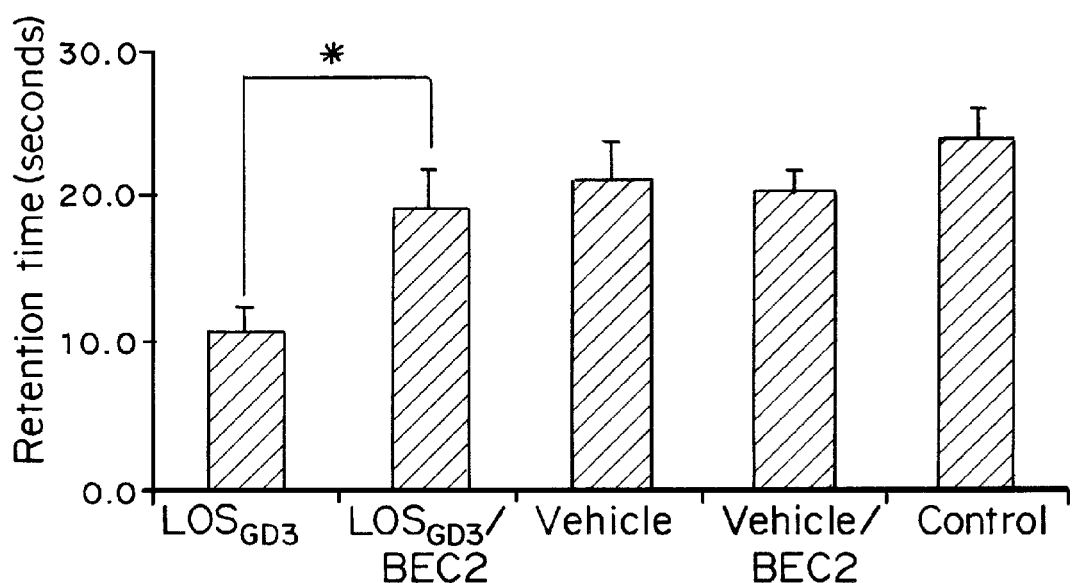
FIG. 5B is a bar graph showing rotarod retention time (sec) 17 weeks after primary immunization by $LOS_{GD3}$ (first bar), $LOS_{GD3}$/BEC2 (second bar), Vehicle (third bar), Vehicle/BEC2 (fourth bar), and Control (fifth bar).

FIG. 5 shows the effect of BEC2 on NCV and rotarod performance of animals undergoing treatment. As shown in FIG. 5A, the effect of BEC2 on NCV at week 0 and week 16 after primary immunization by $LOS_{GD3}$. NCVs was measured at week 0 and at week 16 for each group of animals; $LOS_{GD3}$, $LOS_{GD3}$/BEC2, vehicle, vehicle/BEC2, and control (nontreatment). Values are means±SD for four animals. The values were analyzed by one-way ANOVA followed by Tukey's multiple-comparison tests (<0.01). The asterisk denotes statistical significance (*P<0.01) estimated by Dunnet's multiple-comparisons test. As shown in FIG. 5B, the effect of BEC2 on motor performance on the rotarod test. At 17 weeks after primary immunization, the rotarod test was performed for five experimental animal groups: $LOS_{GD3}$, $LOS_{GD3}$/BEC2, vehicle, vehicle/BEC2, and control (nontreatment). Values are means±SD for four animals. The data values were analyzed by one-way ANOVA followed by Tukey's multiple-comparisons test (<0.01). The asterisk denotes statistical significance by Dunnet's multiple-comparisons test (*P<0.01).

Example 7

Rotarod Test

Materials and Methods
Rotarod Motor Test

The rotarod motor test was performed according to the procedure of Geralai et al. (Dunham and Miya, 1957. *J Am Pharm Assoc Am Pharm Assoc* 46: 208-209; Jones and Roberts, 1968. *J Pharm Pharmacol* 20: 302-304). A rat was placed on a rotating roller (4 cm in diameter), and the time for which the rat remained on the roller was measured. The test included eight trials; each trial was performed at an interval of 10 min; four trials were performed. An additional four trials were conducted after 24 hr. When the rat could stay on the rotating rod at a constant speed of 5 rpm for a cumulative duration of at least 2 sec, the rotation speed was increased by 0.2 rpm/sec.

Results

Animals underwent a rotarod test at the endpoint according to the experimental schedule of treatments. There was no statistically significant difference in retention time between the vehicle and untreated control groups (FIG. 5B). $LOS_{GD3}$-treated animals had muscle weakness, with significantly shorter retention in all the experimental rats (P<0.01). There was a statistically significant difference in improved rotarod performance between the BEC2 treatment group and the $LOS_{GD3}$ treatment group.

Example 8

Morphological Analysis of Motor Neurons and Motor Axons

Materials and Methods
Histological/Morphological Examination

Pathological examination was undertaken to correlate changes with clinical manifestations in the animals. At the endpoint (week 18) of animal experimentation (FIG. 2), the animals were sacrificed. After a blood sample was withdrawn from the heart, the animals were perfused with 4% paraformaldehyde in PBS buffer via the arcus aortae. After perfusion, the lumbar spinal cord was dissected and sectioned into four to six transverse segments spaced 1 mm apart. The right sciatic nerves also were carefully dissected from their origin (5 mm distal to the gluteus maximus) through the distal branch point at the peroneal and tibial nerves in order to avoid stretching. These nerve sections were placed at 4° C. overnight in a fixative solution containing 4% paraformaldehyde, 2% glutaraldehyde, and 0.1 M sodium cacodylate buffer (pH 7.4). After the nerves were washed three times in cacodylate buffer (pH 7.4), they were postfixed at 4° C. with 2% osmium tetroxide/0.1 M sodium cacodylate buffer (pH 7.4) for 60 min, dehydrated in graded ethanol, stained at 4° C. with 2% uranyl acetate/70% ethanol for 30 min, and embedded in epoxy resin (Poly/Bed 812; Polysciences, Warrington, Pa.). One-micrometer-thick cross-sections of nerve were stained with toluidine blue for histological examination using an Axiophot photomicroscope equipped with an Axiocam (Carl Zeiss, Jena, Germany). Images were stored and analyzed using AxioVision. The total number of myelinated fibers in each nerve was assessed by visual counting. Myelination-to-myelinated area ratio was calculated in Scion Image software. The total fiber area and the total myelin area were masked and automatically quantitated by the program. In total five images were analyzed per cross-section, and the percentage of myelinated area was determined by using the following formula: myelin %=(myelinated area/total area)×100. For electron microscopy, ultrathin sections were prepared and examined by a high-performance, high-contrast, 40-120-kV transmission electron microscope (JEOL JEM-1230).

Immunofluorescence Analysis of NMJ

Adult rats were anesthetized with pentobarbital and then perfused with 2% paraformaldehyde in 0.01 M PBS buffer. Diaphragms were excised and frozen in liquid nitrogen. Cryosections (10 μm) were double immunostained with mAb R24 and antineurofilament polyclonal rabbit antibody (50-100 μg/ml) in a blocking buffer containing 10% BlockAce (Dainippon Pharmaceutical, Osaka, Japan) in normal goat serum at 50-100 μg/ml for 30 min at room temperature and developed with the following secondary antibodies for 60 min at 4° C.: anti-mouse IgG conjugated to Alexa Fluor 488 (1:20; Sigma) and anti-rabbit IgG conjugated to Alexa Fluor 350 (1:100; Vector, Burlingame, Calif.). Motor end-plates were simultaneously labeled with α-bungarotoxin conjugated to Alexa Fluor 594 (0.5 µg/ml; Molecular Probes, Eugene, Oreg.). Immunostained sections were mounted on slides, covered with microslips, and observed with an Olympus laser scanning confocal microscope (Fluoview BX50; Olympus) at a wavelength of 488 nm or 543 mm.

Results

Animals were examined for structural alterations and pathological changes of the motor spinal cord neurons and sciatic nerves in $LOS_{GD3}$-treated rats. Within the lumbar spinal cord, there were no overt structural differences between the anterior horn cells in the untreated control group and the $LOS_{GD3}$-treated rats. LOS treatment resulted in changes in toluidine blue staining, which revealed myelin. The sciatic nerve change was detected by EM analysis. Treatment with BEC2 caused clear improvement in demyelination based on morphological analysis. Profile counts (numbers of large cells in the anterior horn/cross-section) indicated similar densities of lumbar motor neurons between the control (nontreatment) and the $LOS_{GD3}$-treated rats (31±5 vs. 34±4 neurons/section, N=4, respectively). There was no difference between the control and the $LOS_{GD3}$-treated rats in the neuronal profile area (302±15 µm$^2$ vs. 298±21 µm$^2$, N=4, respectively).

To assess for morphologic alterations corresponding to motor dysfunction or muscle weakness evaluated by NCV measurement and rotarod tests, distal motor nerves were examined near the tibial branch in the sciatic nerve. This nerve contains predominantly myelinated motor fibers that serve skeletal muscle fibers of the lower distal leg. There was a noticeable change in myelin thickness and a statistically significant difference between the control and the $LOS_{GD3}$-treated groups in the percentage of myelinated area in the myelinated fiber (control, 36±5.2%; $LOS_{GD3}$, 12.8±4.8%; P<0.01.

Monoclonal antibody R24 (anti-GD3) immunostained motor nerve terminals. GD3 was localized in the presynaptic area of the neurons together with NF, and the staining of t %-bungarotoxin was localized in postsynaptic membrane. Despite a generally diffuse staining of the presynaptic area by anti-GD3, a condensed localization of GD3 at the NMJ was shown in the white-colored segment, which was costained by α-bungarotoxin, anti-NF, and anti-GD3.

Example 9

Inhibition of NMJ Activity

Materials and Methods
NMJ Activity

Spinal cord-muscle coculture was performed according to the method of Taguchi et al. (2004. *J Neurol Sci* 225: 91-98). Briefly, muscle and spinal cord explants cells were prepared from muscle and spinal cord tissues (containing dorsal root ganglia), respectively, of 17-day-old fetal rats. Muscle cells and spinal cord explants were cocultured and maintained for up to 1 week in the medium (67% Dulbecco's modified Eagle's medium and 23% medium 199) containing 10% fetal calf serum supplemented with 25 ng/ml fibroblast growth factor and 20 µg/ml insulin. Functional NMJ formation was observed by an inverted microscope (IX-70; Olympus, Tokyo, Japan) with an experimental chamber on the stage. The preparation was perfused continuously with the medium at a rate of 1-2 ml/min. Spontaneous muscle action potential frequency was recorded by a glass microelectrode (Ag/AgCl, 30-40 MΩ) and a recording electrode (3 M KCl). The recording system was a Microelectrode Amplifier MEZ-8301, Memory Oscilloscope VC-11 (Nihon Kohden, Tokyo, Japan), and an A-D Converter DigiData 1200 Interface (Axon Instruments, Union City, Calif.). The spontaneous muscle action potential was low-pass filtered at 1 kHz. An antiserum solution, 10 was delivered directly near the innervated muscle cells with a micropipette.

Results

Figure 6A:
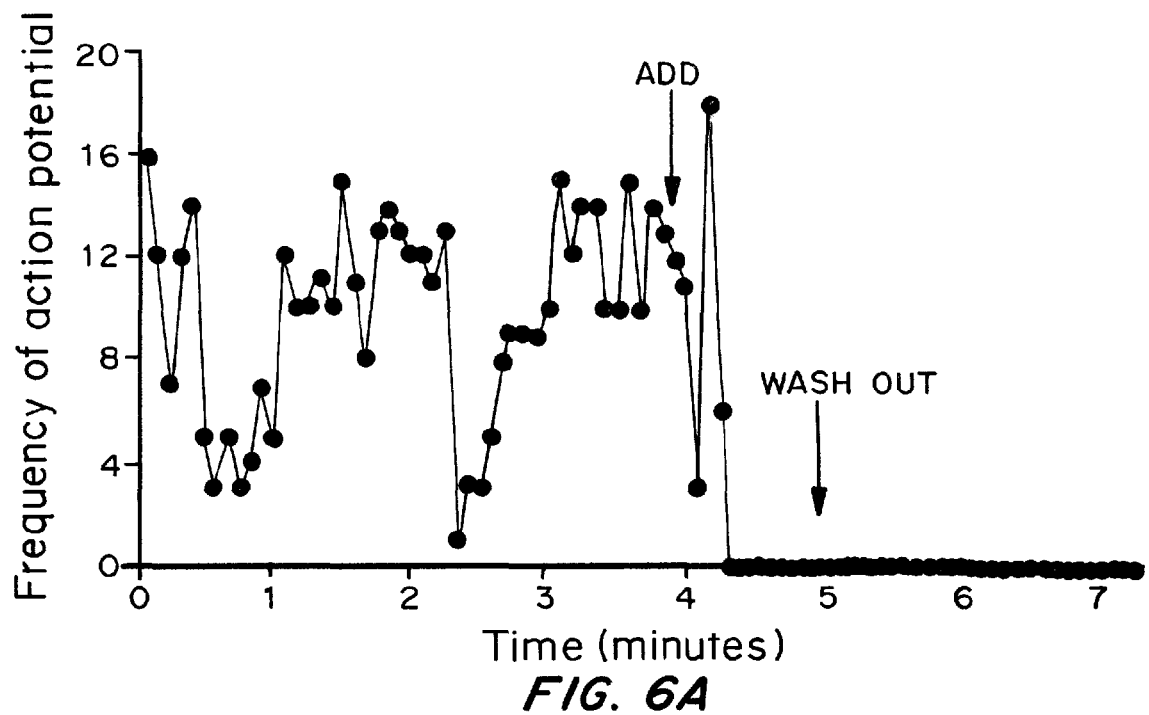
FIGS. 6A-6C are graphs showing spontaneous muscle action potential frequencies (every 5 sec.) in spinal cord-muscle cocultured cells administered serum from rats immunized with $LOS_{GD3}$ (FIG. 6A), $LOS_{GD3}$ (serum subjected to immunoabsorption by GD3) (FIG. 6B), or $LOS_{GD3}$/BEC2
Figure 6B:
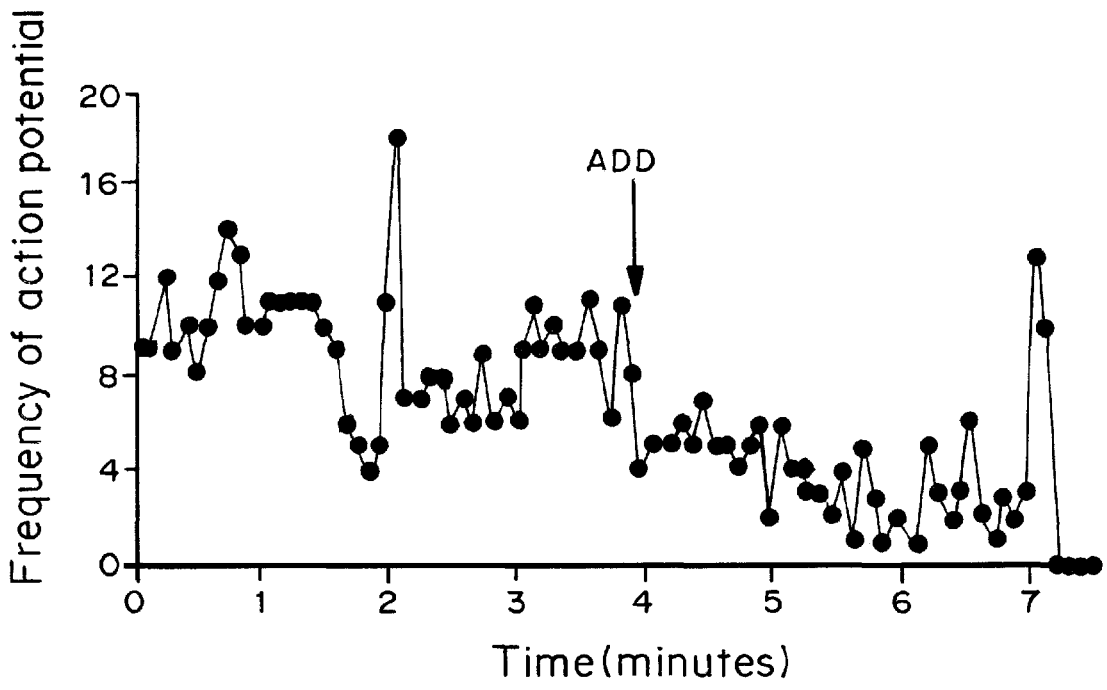
Figure 6C:
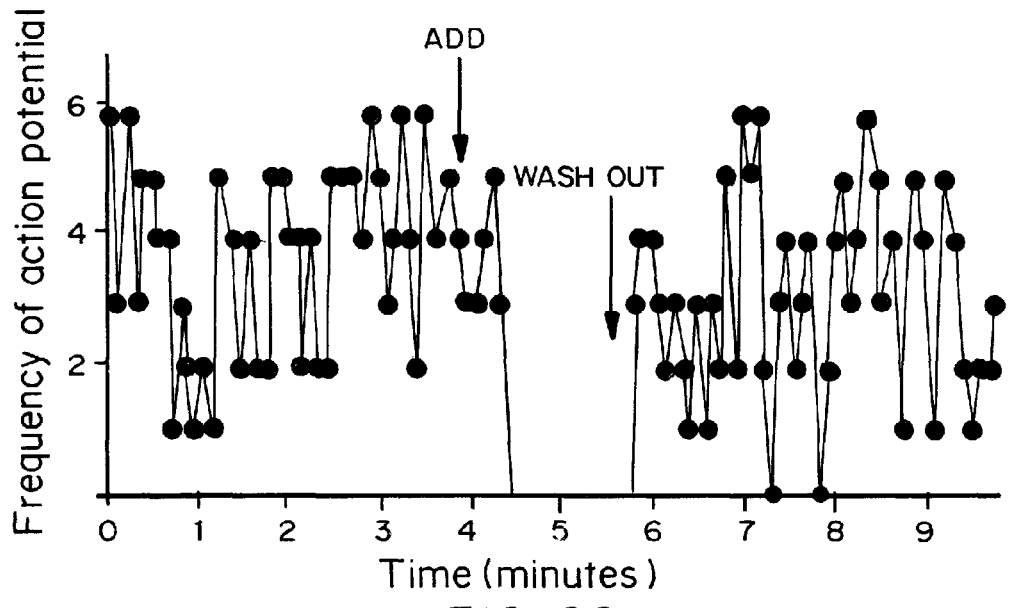

To determine the nature of the anti-GD3 antibody produced in $LOS_{GD3}$-sensitized rats with neuromuscular weakness, spontaneous muscle action potential frequencies were examined by addition of the serum to a coculture system of spinal cord-muscle cells. Those treated with $LOS_{GD3}$ showed a strong blockade of NMJ action potential frequencies immediately after addition of the serum (FIG. 6A). This inhibitory activity, however, could be abolished from the serum after immunoabsorption with GD3 as shown by $LOS_{GD3}$ (+absorption; FIG. 6B). The $LOS_{GD3}$/BEC2 serum showed an immediate strong blockade of NMJ action potential frequencies, but the blockade was reversibly removed by the washing-out procedure, and the NMJ activity recovered (FIG. 6C).

FIG. 6 shows the time course of inhibitory effect on spontaneous muscle action potential frequencies in spinal cord-muscle cocultured cells. The frequencies were recorded every 5 sec. Arrows show addition of 10 µl rat serum and washing out. Each serum sample was obtained from four rats, in three groups. One of the four sera was used for addition to the assay system for spontaneous muscle action potential activity. This absorbed serum was examined in the assay system for spontaneous muscle action potential activity.

Example 11

Competitive Inhibition Assay

Materials and Methods
Streptavidin-Coated ELISA for Determination of Plasma $bP_{GD3}$-4 Levels Plasma containing $bP_{GD3}$-4 was attached to streptavidin-coated 96-well polystyrene plates obtained from Pierce (No. 15121, Rockford, Ill., USA), and ELISA was performed according to the manufacturer's instructions. The efficacy of binding of the anti-GD3 antibody to immobilized $bP_{GD3}$-4 was determined using mAb R24, followed by an anti-mouse horseradish peroxidase-conjugated secondary antibody and colorimetric development. Briefly, the plasma samples from the single-dose administration of $bP_{GD3}$-4 were applied to the streptavidin-coated ELISA plates at serial double dilutions in 1% bovine serum albumin/phosphate buffered-saline (BSA/PBS) solution. The plate was incubated for 1 h at room temperature, and after washing with 1% BSA/PBS buffer, each well of the plate was treated with the mAb R24 (1 µg/mL in 1% BSA/PBS buffer). After washing with 1% BSA/PBS buffer, each well was treated with an anti-mouse IgG horseradish peroxidase-conjugated antibody (Jackson ImmunoResearch Lab, West Grove, Pa., USA). This secondary antibody was pre-treated with rat IgG to eliminate contamination from any anti-rat IgG binding activity. Finally, the bound secondary antibody was visualized by a color-generating reagent (OPD Peroxidase Substrate in PBS; Sigma, St Louis, Mo., USA). Half-saturation absorbance values for plasma samples were estimated by serial plasma dilution curves of ELISA. The absorbances were then converted into values of plasma concentration using a standard serial dilution curve of rat serum containing authentic $bP_{GD3}$-4.

Results

GD3-like peptide mimics ($P_{GD3}$-1 to $P_{GD3}$-6) were tested by ELISA for competitive inhibition of GD3 reactivity to mAb R24. Four peptides ($P_{GD3}$-3, $P_{GD3}$-4, $P_{GD3}$-5, and $P_{GD3}$-6) revealed remarkable inhibitory activities (FIG. 8); the $IC_{50}$ values were 300 pmol/mL for $P_{GD3}$-3, 150 pmol/mL for $P_{GD3}$-4, 100 pmol/mL for $P_{GD3}$-5, and 250 pmol/mL for $P_{GD3}$-6. In contrast, $P_{GD3}$-1 and $P_{GD3}$-2 had little or no inhibitory activity. The active peptides showed full inhibition of GD3 binding to mAb R24 at a concentration of more than 600 pmol/mL and were used for further study.

FIG. 8 illustrates the effect of GD3-like peptides on binding of R24 mAb to GD3 by ELISA. Each of the GD3-peptide mimics in solution ($P_{GD3}$-1, $P_{GD3}$-2, $P_{GD3}$-3, $P_{GD3}$-4, $P_{GD3}$-5, or $P_{GD3}$-6) was incubated with R24 mAb for 30 min at room temperature at various concentrations as indicated in the horizontal axis. An aliquot of the mixtures (100 μL), was added to each well of an ELISA plate coated with 0.1 μg of GD3. The remaining binding activity of R24 mAb was measured by ELISA. Values are mean±SEM, n=6 individual experiments.

Example 12

Pharmacokinetic Study

Materials and Methods
Biotinylation of $P_{GD3}$-4
One of the GD3-like peptides ($P_{GD3}$-4) was biotinylated using an EZ-Link® Sulfo-NHS-LC-Biotinylation Kit (Pierce, Rockford, Ill.). Ten mg of $P_{GD3}$-4 was dissolved in 2 mL of PBS according to the instruction kit. After addition of the Sulfo-NHS-LC-Biotin solution, the reaction mixture was incubated for 1 h at room temperature. The biotinylated product ($bP_{GD3}$-4) was purified by a Zeba™ Desalt Spin Column. The biotin-peptide ratio of $bP_{GD3}$-4 was determined using a HABA (4'-hydroxyazobenzene-2-carboxylic acid) Biotin Quantitation Kit (Pierce, Rockford, Ill.) and a LavaPep™ Peptide Quantification Kit (Fluorotechnics, Sydney, Australia), and was expressed as nmol biotin/nmol peptide.

Pharmacokinetic Analysis
A Micro-Renathane polyurethane cannula, 0.84 mm o.d.× 0.36 mm i.d., (Braintree Scientific Inc., Braintree, Mass.) was inserted before dosing into the femoral vein of a female Lewis rat (n=9; body weight=200±20 g). A single dose of $bP_{GD3}$-4 (100, 500, or 1000 nmol $kg^{-1}$; n=3 per group) was administered i.p. Serial blood samples (~200 μL) were taken from the femoral vein for $bP_{GD3}$-4 testing at predose (0 h) and serial postdose-time points (0.5, 1, 2, 3, 6, 12, and 24 h). Blood samples were centrifuged at room temperature and the plasma harvested. The plasma samples were stored at −60° C. to −80° C. until analyzed by a streptavidin-coated ELISA plate for determining the total concentration of $bP_{GD3}$-4.

The plasma concentration-time course data of $bP_{GD3}$-4 were analyzed by a noncompartmental method of i.p. administration with first-order output as previously reported (Barrett et al., 1997; Wahl et al., 1988). The following parameters were calculated: maximum-, minimum-, and average-observed plasma concentration ($C_{max}$, $C_{min}$, and $C_{av}$), areas under the plasma concentration-time curve from zero to infinite time (AUC) plasma clearance (CL), distribution half-life ($t_{1/2\alpha}$), and elimination half-life ($t_{1/2\beta}$). Calculations of rate constants $t_{1/2\alpha}$ and $t_{1/2\beta}$ were obtained by the curve-peeling method (Gibaldi and Perrier, 1982). AUC was estimated according to the method of the trapezoidal rule by including the remaining AUC after the last measurable time point (24 h), and extrapolating the curve from the last time point to infinity.

GD3-Like Peptides
The GD3-like peptides were synthesized in the W. M. Keck Biotechnology Resource Center, Yale University (New Haven, Conn., USA), based on the peptide sequences reported previously (Willers et al., 1999. Peptides 20:1021-1026; Popa et al., 2006. FEBS Lett. 580:1398-1404), shown in Table 2. The peptide sequences of $P_{GD3}$-1, $P_{GD3}$-2, $P_{GD3}$-3, and $P_{GD3}$-4 were initially reported (Popa et al., 2006. FEBS Lett. 580:1398-1404). Two other peptides, $P_{GD3}$-5 and $P_{GD3}$-6, were synthesized based on data reported by Willers et al., (Willers et al., 1999. Peptides 20:1021-1026).

TABLE 2

GD3-like peptide

| Peptide | Amino acid sequence | |
|---------|---------------------|---|
| PGD3-1 | LAPPRPRSELVFLSV | SEQ ID NO: 1 |
| PGD3-2 | PHFDSLLYPCELLGC | SEQ ID NO: 2 |
| PGD3-3 | GLAPPDYAERFFLIS | SEQ ID NO: 3 |
| PGD3-4 | RHAYRSMAEWGFLYS | SEQ ID NO: 4 |
| PGD3-5 | ACTPYAMLPGCK | SEQ ID NO: 5 |
| PGD3-6 | SVAVPPPADDPSWRY | SEQ ID NO: 6 |

Results

The dosage schedule of the 4 active peptides ($P_{GD3}$-3, $P_{GD3}$-4, $P_{GD3}$-5, and $P_{GD3}$-6) was designed by pharmacokinetic analysis based on a single dose administration into a rat. To assist in quantitation of the peptide mimics, $P_{GD3}$-4 was biotinylated and the specific activity for biotin labeling was determined as 0.4 for $bP_{GD3}$-4 (mole of biotin per mole of peptide).

Purified $bP_{GD3}$-4 was administered i.p. to rats as described above. Plasma concentration versus time after a single dose of 100, 500, and 1,000 nmol $kg^4$ for $bP_{GD3}$-4 are in FIG. 12A. None of the experimental rats died or exhibited toxicity as a result of the peptide administration.

Table 3 lists the parameter values obtained from a noncompartmental analysis of $bP_{GD3}$-4. Concentration over time data showed two-phase attenuation of distribution and elimination expressed as $t_{1/26\alpha}$, and $t_{1/2\beta}$. There was no change of parameter values for clearance, $t_{1/2\alpha}$, and $t_{1/2\beta}$, in the single-dose range of 100-1000 nmol $kg^{-1}$ for $bP_{GD3}$-4. From these data, $bP_{GD3}$-4 exhibits linear pharmacokinetics after multiple doses. Elimination was rapid necessitating multiple dosing in order to determine the kinetics. In light of the $t_{1/2\beta}$ and minimum effective plasma concentrations determined from a single dose of $bP_{GD3}$-4, we adopted a chronic i.p. dose administration of $P_{GD3}$-4 (1,000 nmol $kg^{-1}$ at 24-hourly intervals for 7 days). And, in order to avoid the effects of multiple i.p. dosing, the animals were rested at two-week intervals. As shown in the chronic simulation (FIG. 12B), the resulting $C_{max}$, $C_{min}$, and $C_{av}$ were $0.67 \times 10^3$, 0.33, and $0.34 \times 10^3$ nmol/mL, respectively. At a minimum, an effective plasma concentration of peptides was achieved by multiple dosing, and this is shown by the $IC_{50}$ values for each of the active peptides (0.3 nmol/mL for $P_{GD3}$-3, 0.15 nmol/mL for $P_{GD3}$-4, 0.1 nmol/mL for $P_{GD3}$-5, and 0.25 nmol/mL for $P_{GD3}$-6) (FIG. 2).

TABLE 3

Pharmacokinetic parameters after i.p. administration of bPGD3-4 to normal Lewis rats

| Parameter | | bPGD3-4 dose group | | |
|---|---|---|---|---|
| | | n = 3 | n = 3 | n = 3 |
| Dose | (nmol kg$^{-1}$) | 100.0 | 500.0 | 1000.0 |
| tmax | (hr) | 0.5 | 0.5 | 0.5 |
| Cmax | (nmol mL$^{-1}$) | 70.8 (10.0) | 267.1 (52.1) | 667.2 (121.1) |
| t$_{1/2\alpha}$ | (hr) | 0.48 (0.03) | 0.42 (0.03) | 0.46 (0.03) |
| t$_{1/2\beta}$ | (hr) | 2.45 (0.27) | 2.45 (0.33) | 2.76 (0.42) |
| CL | (mL hr$^{-1}$) | 0.82 (0.24) | 0.86 (0.11) | 0.71 (0.04) |
| Vdss | (mL) | ND | ND | ND |
| AUC | (nmol mL$^{-1}$ hr) | 130.0 (43.6) | 589.2 (72.9) | 1425.7 (78.8) |

The values are the mean (SD)
ND, not determined.
Vdss, steady-state of distribution.

Figure 12A:
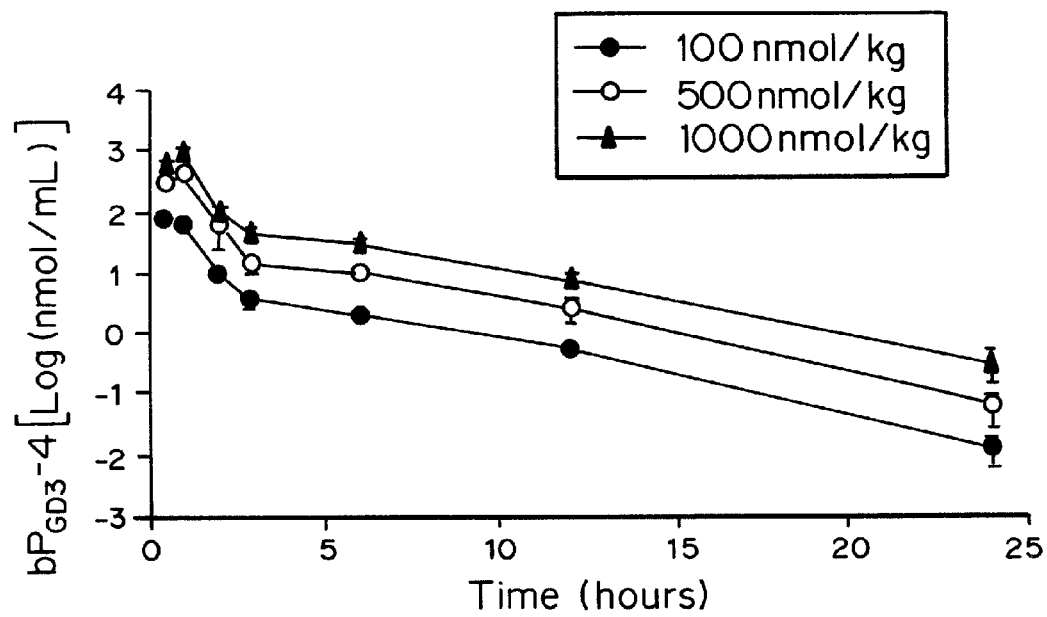
FIG. 12A is a graph showing the mean plasma concentration of $bP_{GD3}$-4 (Log(nmol/ml)) in rats as a function of time (h) following i.p. single dosing with 100 nmol/kg (closed circle), 500 nmol/kg (open circle), or 1000 nmol/kg (triangle) $bP_{GD3}$-4.
Figure 12B:
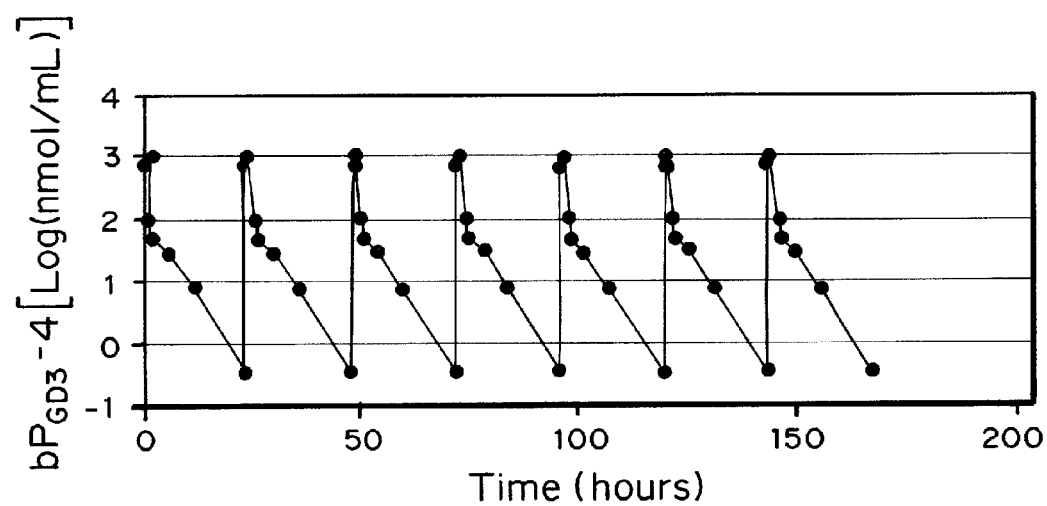
FIG. 12B is a graph simulating concentration of $bP_{GD3}$-4 (Log(nmol/ml)) as a function of time (h) following dosing with 1000 nmol/kg $bP_{GD3}$-4 daily for 7 days.

FIG. 12A shows mean plasma concentration-time profiles following i.p. single dosing with 100 nmol kg$^{-1}$ (circle), 500 nmol kg$^{-1}$ (triangle) of bP$_{GD3}$-4. n=3 rats; values are means±SD. FIG. 12B shows expected plasma concentration-time profile simulated from multiple administration 1000 nmol kg$^{-1}$ of bP$_{GD3}$-4 in by time intervals of 24-hourly for 7 days. The simulation-plot was drawn according to the method of the trapezoidal rule of AUC and the parameters including t$_{1/2\beta}$ values for 1000 nmol kg$^{-1}$ of bP$_{GD3}$-4 as shown in Table 3. The plasma concentrations of bP$_{GD3}$-4 in FIG. 12A and FIG. 12B are shown on a logarithmic scale on the vertical axis.

Example 13

Experimental Animals

Figure 7:
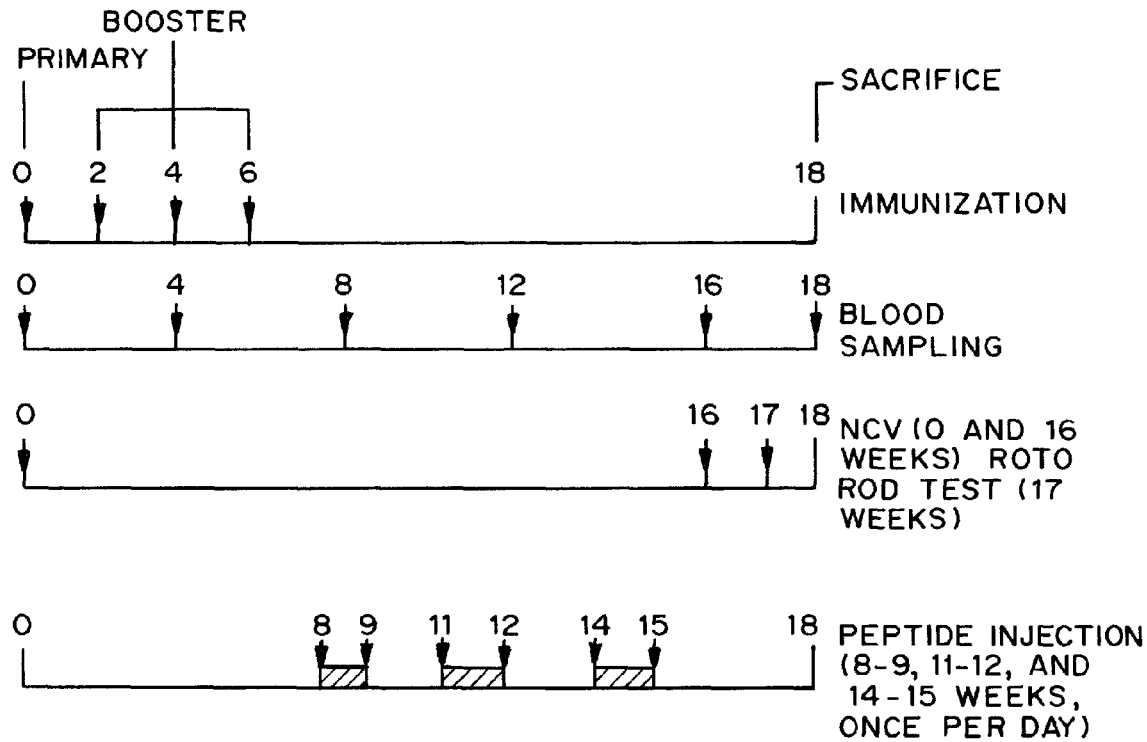
FIG. 7 is a diagram showing the experimental schedule for animal treatments with $LOS_{GD3}$ and GD3-like peptides.
Figure 8A:
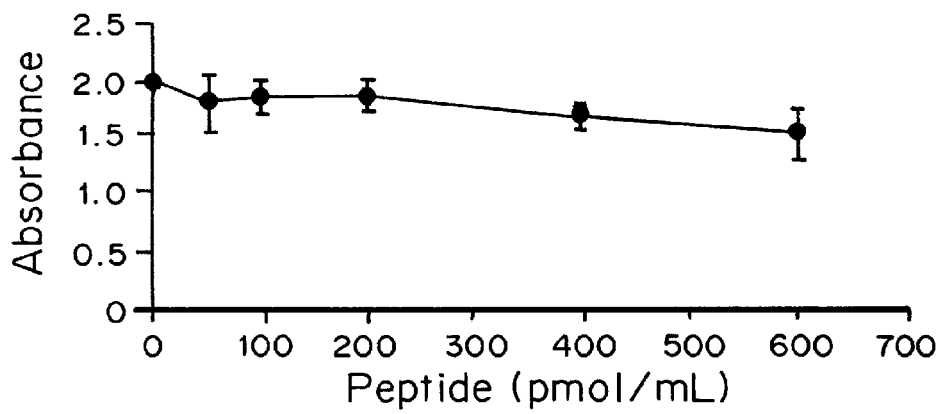
FIGS. 8A-8F are graphs showing absorbance in an ELISA plate coated with 0.1 μg GD3 as a function of the concentration (pmol/ml) of the GD3-like peptides $P_{GD3}$-1 (FIG. 8A), $P_{GD3}$-2 (FIG. 8B), $P_{GD3}$-3 (FIG. 8C), $P_{GD3}$-4 (FIG. 8D), $P_{GD3}$-5 (FIG. 8E), or $P_{GD3}$-6 (FIG. 8F) incubated with MAb R24 prior to addition to the ELISA wells.
Figure 8B:
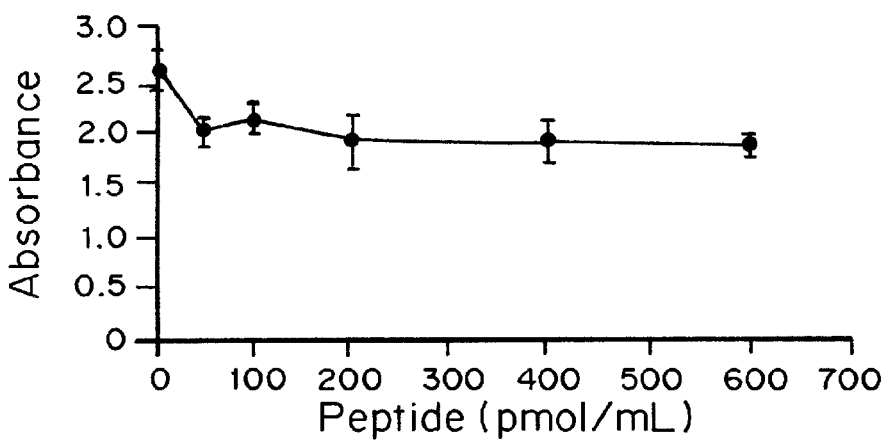
Figure 8C:
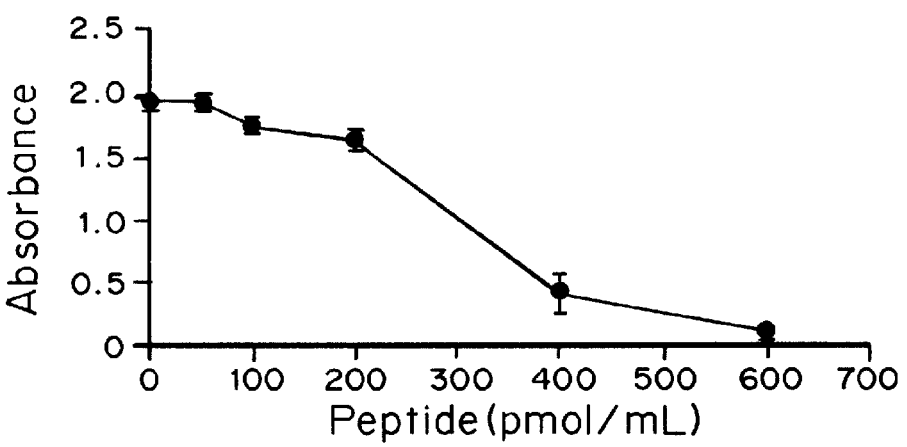
Figure 8D:
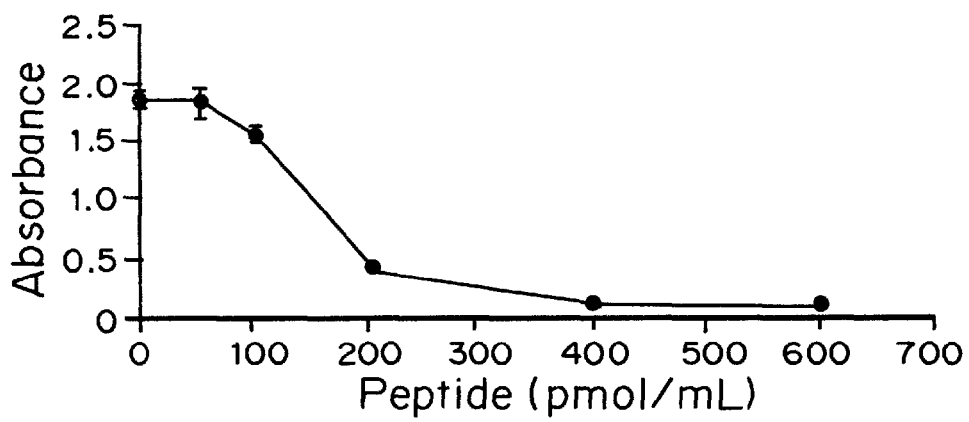
Figure 8E:
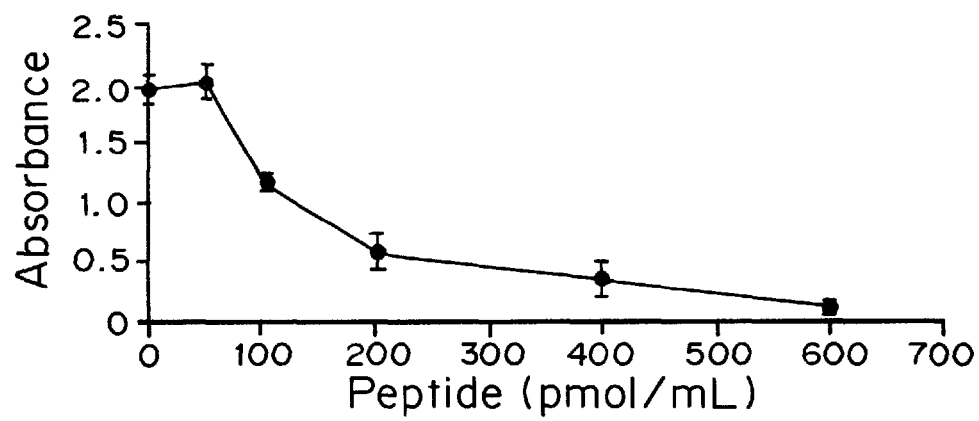
Figure 8F:
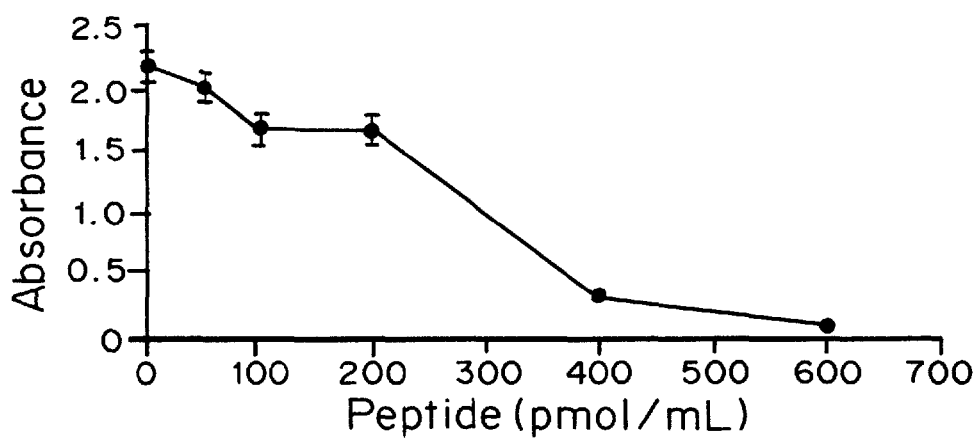

Materials and Methods
Animal Experimental Protocol
Immunization was performed according to an established procedure (Usuki et al., 2006. *J. Neurosci. Res.* 83:274-284) and the scheme is shown in FIG. 7. Twelve-week-old female Lewis rats, weighing 200-220 g each, were used. One hundred micrograms of LOS$_{GD3}$ was dissolved in 50 mM PBS buffer as vehicle, and with 0.05 mL of keyhole limpet hemocyanin (2 mg/mL) emulsified with an equal volume of complete Freund's adjuvant. A single subcutaneous injection of 0.1 mL of inoculum (or vehicle) was made into the rats' shoulders and hind limb footpads. Additional booster injections were administered similarly to LOS$_{GD3}$-(or vehicle-) treated animals at 2-week intervals with 100 μg of LOS$_{GD3}$ (or no additive) and 2 mg/mL of keyhole limpet hemocyanin in PBS emulsified with an equal volume of incomplete Freund's adjuvant after 6 weeks. Forty-four experimental animals were grouped into 10 treatment paradigms (n=4 each): (i) LOS$_{GD3}$, (ii) LOS$_{GD3}$/P$_{GD3}$-3, (iii) LOS$_{GD3}$/P$_{GD3}$-4, (iv) LOS$_{GD3}$/P$_{GD3}$-5, (v) LOS$_{GD3}$/P$_{GD3}$-6, (vi) vehicle, (vii) vehicle/P$_{GD3}$-3, (viii) vehicle/P$_{GD3}$-4, (ix) vehicle/P$_{GD3}$-5, and (x) LOS$_{GD3}$/P$_{GD3}$-6. The remaining four animals were the untreated control group (n=4). As shown in the fourth stepladder of FIG. 7, the rats were subjected to daily i.p. injections of a peptide: 1000 nmol/kg, three times from 8, 11, and 14 weeks for 3 weeks, including a 2-week rest.

The timing of treatment and performance tests between week-0 and week-18 in the experimental period are shown in FIG. 7. Forty-four experimental animals were grouped into 10 treatment groups (n=4 each): (i) LOS$_{GD3}$, LOS$_{GD3}$/P$_{GD3}$-3, (iii) LOS$_{GD3}$/P$_{GD3}$-4, (iv) LOS$_{GD3}$/P$_{GD3}$-5, (v) LOS$_{GD3}$/P$_{GD3}$-6, (vi) vehicle, (vii) vehicle/P$_{GD3}$-3, (viii) vehicle/P$_{GD3}$-4, (ix) vehicle/P$_{GD3}$-5, and (x) LOS$_{GD3}$/P$_{GD3}$-6. The remaining four animals were included as the untreated control group (n=4). As shown on the Bottom line, rats were subjected to i.p. daily injections of a test peptide; 1000 nmol/kg, three times from 8, 11, and 14 weeks for 3 weeks, with 2-week rest intervals. Blood samples were collected retroorbitally by bleeding with a capillary tube at every 4-week intervals (second line below Top). Electrophysiological examination was performed by NCV measurement at week-0 and week-16 (third line below Top). The motor-behavioral performance was performed by rotarod test at week-17 (third line from Top). All animals were killed at the end of week-18.

Before injection of the GD3-like peptide mimics, any endotoxin that might be included in P$_{GD3}$-3, P$_{GD3}$-4, P$_{GD3}$-5, or P$_{GD3}$-6 was removed by ToxinEraser™ Endotoxin Removal Kit (GenScript Corp., Piscataway, N.J., USa), and the endotoxin remaining was detected by the *Limulus* Amebocyte Lysate test (ToxinSensor™ Gel Clot Endotoxin Assay Kit; GenScript Corp.).

Blood samples were drawn retro-orbitally by bleeding with a capillary tube at 0, 4, 8, 12, 16, and 18 weeks after the primary immunization.

All experimental animals were weighed weekly and assessed for clinical signs of peripheral nerve abnormalities. Electrophysiological measurements of nerve conduction velocity (NCV) were performed at 0 and 16 weeks, and motor behavioral-performance by the rotarod test at 17 weeks after the primary immunization. All animals were allowed free access to water and food.

Figure 9:
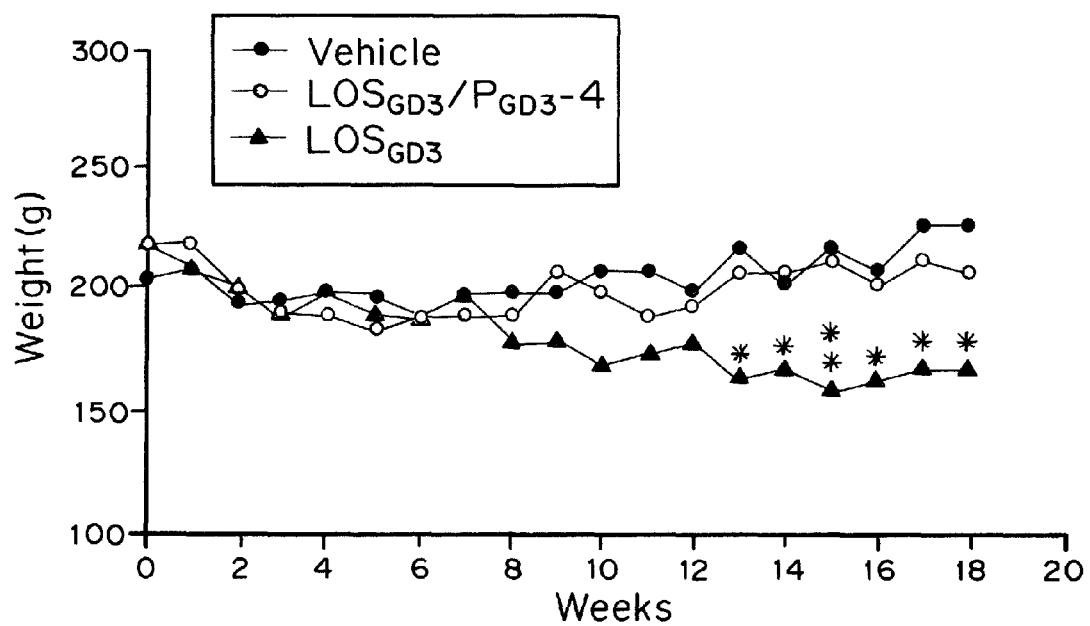
FIG. 9 is a graph showing body weight (g) of rats as a function of time (weeks) after treatment with Vehicle (closed circles), $LOS_{GD3}/P_{GD3}$-4 (open circles), $LOS_{GD3}$ (triangles).

Results
During the course of animal experimentation, the LOS$_{GD3}$-sensitized animals showed mild clinical signs of neurological dysfunction, including a remarkable slowness of movement and noticeable weight loss between 13 and 18 weeks post-treatment as compared to the corresponding vehicle treatment group (FIG. 9). Among the four peptide treatment paradigms, animals treated with P$_{GD3}$-4 revealed a remarkable clinical improvement with lowering of the serum anti-GD3 antibody level, reversal of weight loss and slowing of NCV, and improvement of rotarod performance, as compared with animals treated with P$_{GD3}$-3, P$_{GD3}$-5, and P$_{GD3}$-6. Body weight changes in the three treatment groups (vehicle, LOS$_{GD3}$, and LOS$_{GD3}$/P$_{GD3}$-4) are shown in FIG. 9. Differences between the LOS$_{GD3}$/P$_{GD3}$-4 treatment groups and the LOS$_{GD3}$ treatment group showed statistically significant differences during the period of 13-18 weeks after primary immunization with the LOS$_{GD3}$/P$_{GD3}$-4 animals showing better protection.

FIG. 9 shows changes in body weight after sensitization by LOS$_{GD3}$. The graph shows body weight after vehicle-treatment (closed circle), LOS$_{GD3}$/P$_{GD3}$-4-treatment (open circle), and LOS$_{GD3}$-treatment (triangle) of the week-12 rats. According to Two-Way Anova and Tukey's Test, there is a significant reduction in body weights of the LOS$_{GD3}$-treated group compared with the vehicle-treated group from week-13 to −18 post-treatment. P$_{GD3}$-4 treatment maintained weight at the vehicle-treated group level. There was significant difference of body weight compared LOS$_{GD3}$-treated group by unpaired Student's t-test (*p<0.05, **p<0.01). At the end of the experiment, all animals were killed and the tissues analyzed. There was no adhesive peritonitis or ascites due to infection in animals as a result of administering multiple i.p. doses of the four peptides.

Example 14

Time Course of Anti-GD3 and Anti-LOS$_{GD3}$ Antibody Production

Materials and Methods
Gangliosides
Gangliosides (GM1, GM2, GD1a, GD1b, GT1b, and GQ1b) for an ELISA were prepared from bovine brain tissues in our laboratory. GD3 ganglioside was prepared from bovine buttermilk (Ren et al., 1992. *J. Chem.* 267:12632-12638). The nomenclature of gangliosides is based on that of Svennerholm, 1964. *J Lipid Res.* 5:145-155.

Elisa Assay for IgG Antibodies to Gangliosides and $LOS_{GD3}$

Anti-ganglioside antibody activity was evaluated for GM1, GM2, GD1a, GD1b, GT1b, GQ1b, GD3, and $LOS_{GD3}$ by conventional ELISA as previously described (Usuki et al., 2005. *J. Neurol. Sci.* 232:37-44). To measure half-maximal inhibitory concentrations ($IC_{50}s$) of GD3-like peptides for binding of GD3 to mAb R24, each well of the ELISA plate (Immunlon 1B, Lab System, Franklin, Mass., USA) was coated with 0.1 µg of GD3, and prior to ELISA assay was treated by 1% BSA/PBS solution. The purified mAb R24 IgG (10 µg/mL by 1% BSA/PBS solution) was incubated with various concentrations of GD3-like peptides ($P_{GD3}$-1, $P_{GD3}$-2, $P_{GD3}$-3, $P_{GD3}$-4, $P_{GD3}$-5, and $P_{GD3}$-6) for 30 min. After incubation, the reaction mixture was passed through a 0.22-µm syringe filter (Millipore Corp., Bedford, Mass., USA), and 100 µL of the mixture was added to each well and incubated for 1 h at room temperature. A secondary antibody (horseradish peroxidase-conjugated anti-mouse IgG, 1:5000 dilution in 1% BSA/PBS solution) was applied, incubated for 1 h at room temperature, and visualized by addition of a color-generating reagent (OPD Peroxidase Substrate). The absorbance was measured at 492 nm with a microplate spectrophotometer (BioRad, Hemel Hempstead, UK).

Results

Figure 10A:
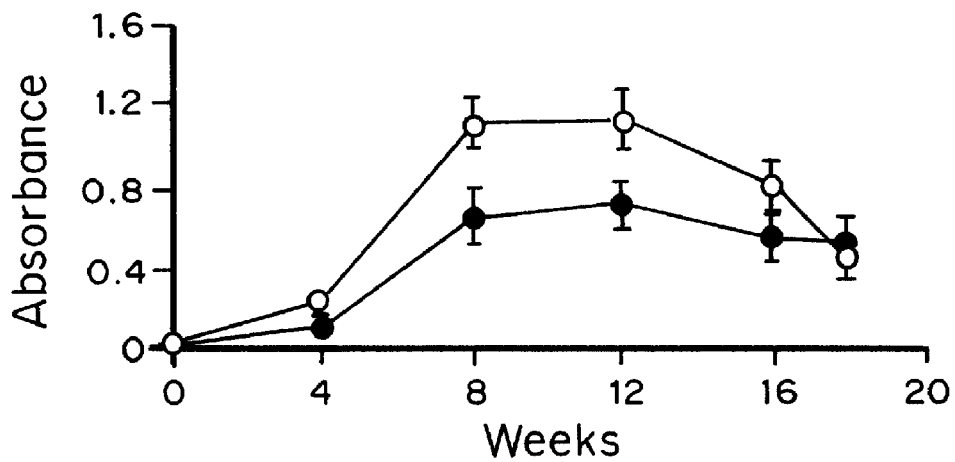
FIGS. 10A-10J are graphs showing serum levels (ELISA absorbance) of anti-GD3 antibody (solid circles) and anti-$LOS_{GD3}$ antibody (open circles) in rats as a function of time (weeks) after administration of $LOS_{GD3}$ (FIG. 10A), $LOS_{GD3}/P_{GD3}$-3 (FIG. 10B), $LOS_{GD3}/P_{GD3}$-4 (FIG. 10C), $LOS_{GD3}/P_{GD3}$-5 (FIG. 10D), $LOS_{GD3}/P_{GD3}$-6 (FIG. 10E), Vehicle (FIG. 10F), Vehicle/$P_{GD3}$-3 (FIG. 10F), Vehicle/$P_{GD3}$-4 (FIG. 10F), Vehicle/$P_{GD3}$-5 (FIG. 10F), and Vehicle/$P_{GD3}$-6 (FIG. 10F).
Figure 10B:
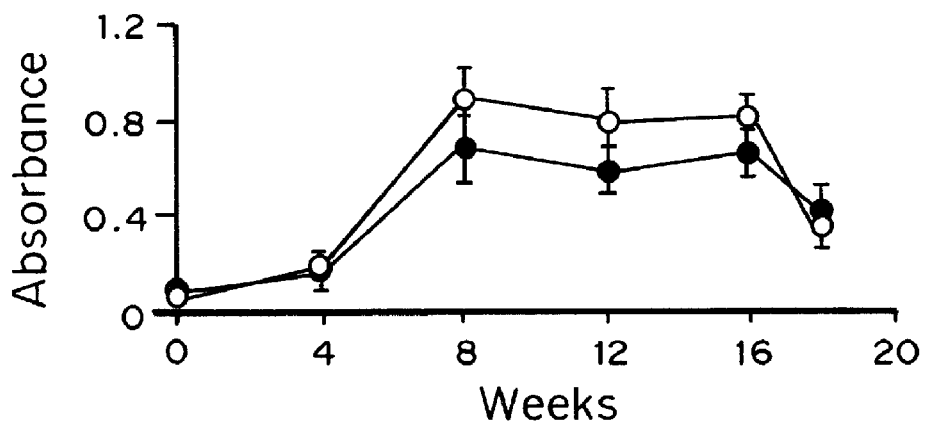
Figure 10C:
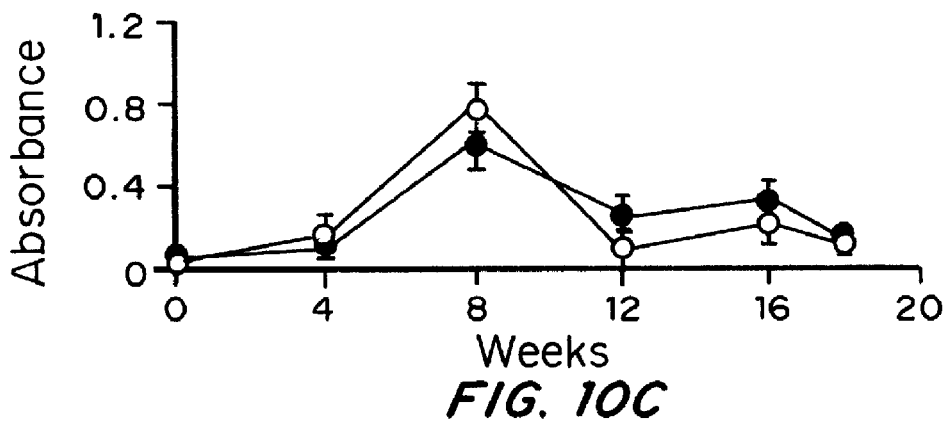
Figure 10D:
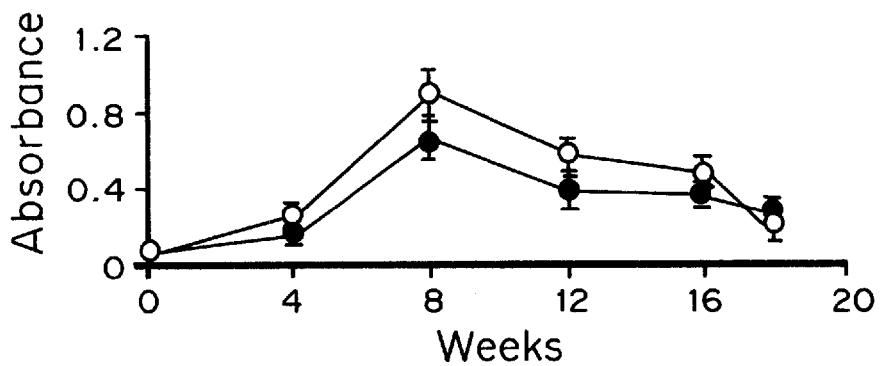
Figure 10E:
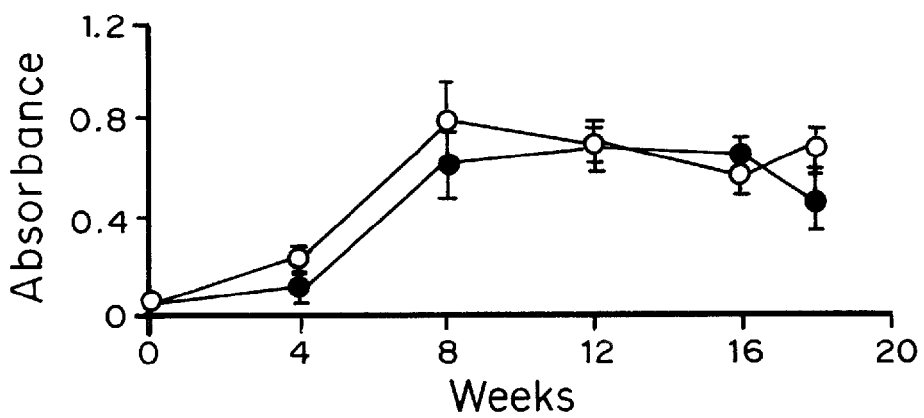
Figure 10F:
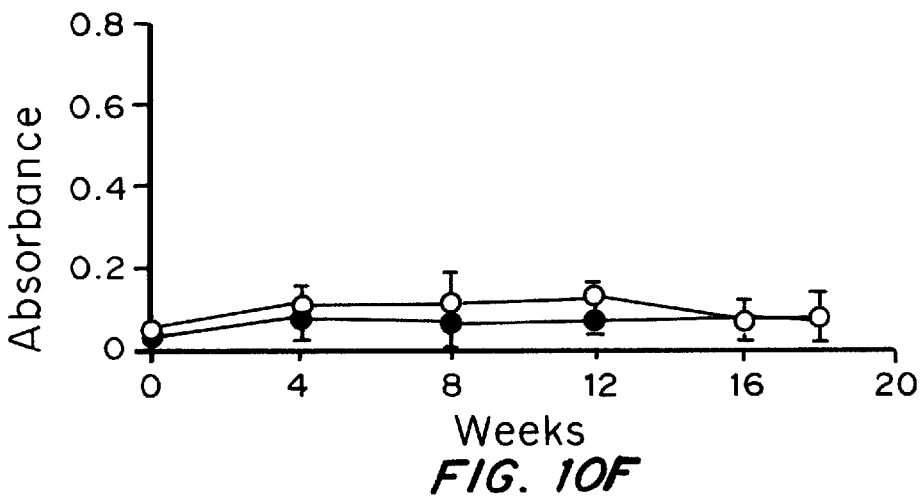
Figure 10G:
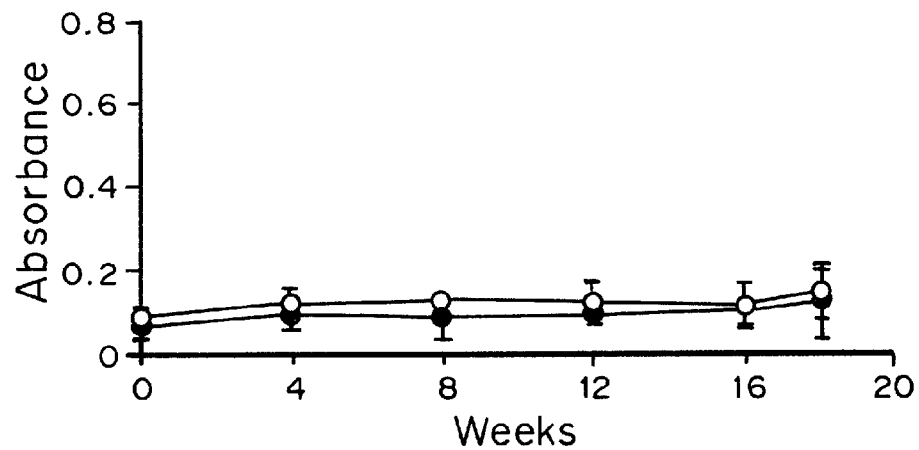
Figure 10H:
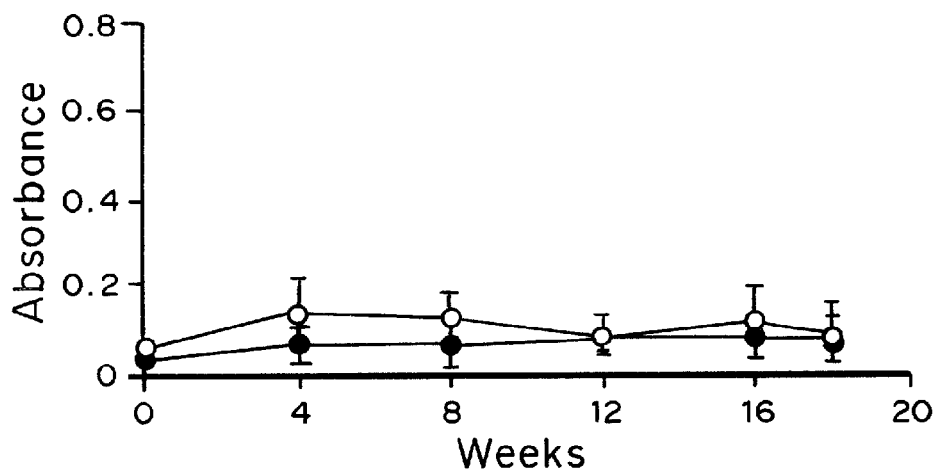
Figure 10I:
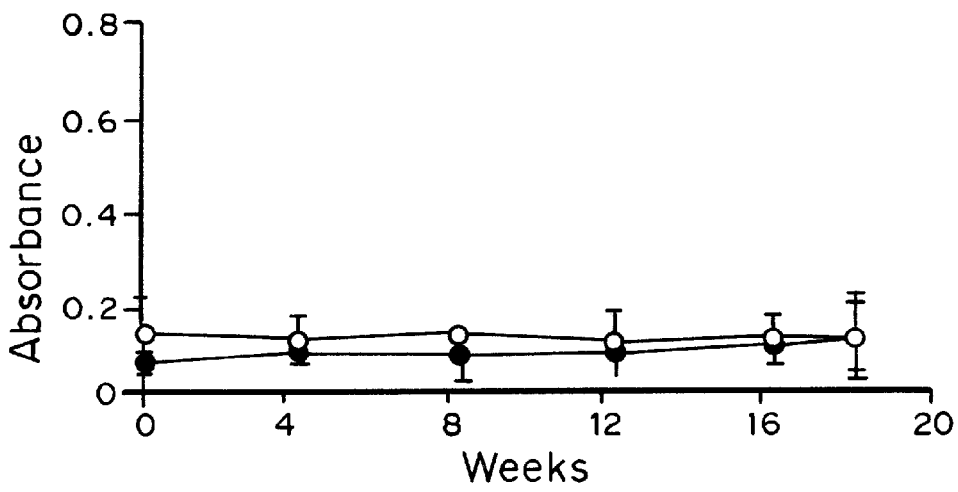
Figure 10J:
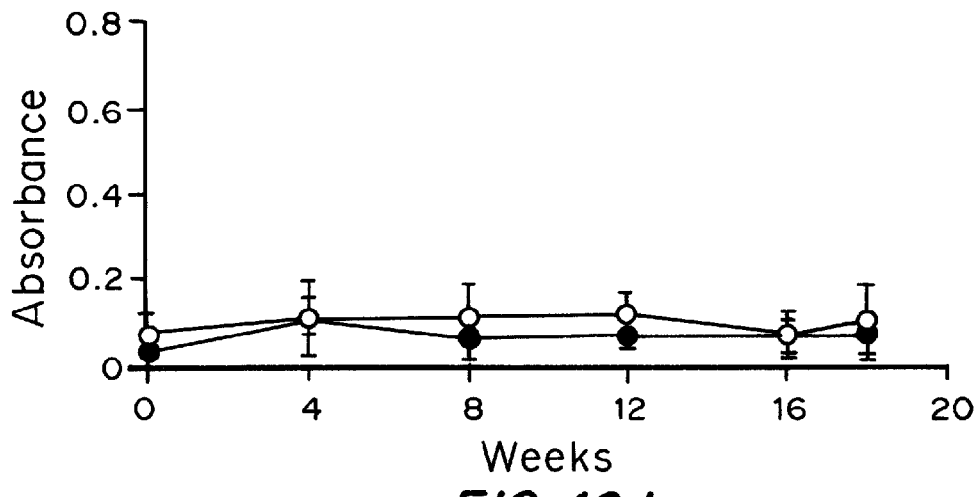

Anti-GD3 and anti-$LOS_{GD3}$ antibody responses following induction of experimental neuritis using $LOS_{GD3}$ were examined periodically during the 18 weeks of experimentation by serum ELISA (samples diluted 1-200 with 1% BSA/PBS buffer) (FIGS. 10A-10J). Other anti-ganglioside antibodies, including anti-GM1, -GM2, -GD1a, -GD1b, -GT1b, and -GQ1b, were not detected in the sera during the entire course of the experiment. The anti-GD3 IgG antibody titer was elevated many fold 8 weeks post-inoculation, in parallel with elevation of the anti-$LOS_{GD3}$ antibody titer (FIG. 10A). The anti-GD3 IgG antibody titer attained and remained at a plateau level (FIG. 10A). There were no IgG antibody responses for GD3 in the vehicle-treated group or in the untreated group (FIG. 10F). In the sera of the animals treated with GD3-like peptides, suppressive effects upon the serum anti-GD3 antibody level varied; the most profound effects were decreased titers to $LOS_{GD3}/P_{GD3}$-4 and $LOS_{GD3}/P_{GD3}$-5 treatment groups (FIGS. 10C and 10D). Two peptides ($P_{GD3}$-4 and $P_{GD3}$-5) were effective in suppressing serum anti-GD3 antibody activity (FIGS. 10C and 10D), whereas no suppression of either anti-$LOS_{GD3}$ or anti-GD3 antibodies was found after chronic treatment with the peptides $P_{GD3}$-3 and $P_{GD3}$-6 (FIGS. 10B and 10E). None of the peptide mimics had any effect on the serum anti-GD3 titer in the vehicle treatment groups (FIGS. 10G-10J).

FIGS. 10A-10J show serum levels of anti-$LOS_{GD3}$ and anti-GD3 antibodies. Animal experimental schedule shown in FIG. 7. Animals bled from week-0 to week-18 at every 4-week interval for serum samples for testing anti-GD3 antibody (closed circle) and anti-$LOS_{GD3}$ antibody (open circle) using ELISA. Values are mean±SD for four animals.

Example 15

NCV Changes

Materials and Methods
Nerve Conduction Velocity

NCVs (m/s) were measured in the rat tail nerve using a Nicolet VikingQuest EMG machine (NeuroCare Group, Madison, Wis., USA) according to the method described previously (Usuki et al., 2006. *J. Neurosci. Res.* 83:274-284).

Results

Figure 11A:
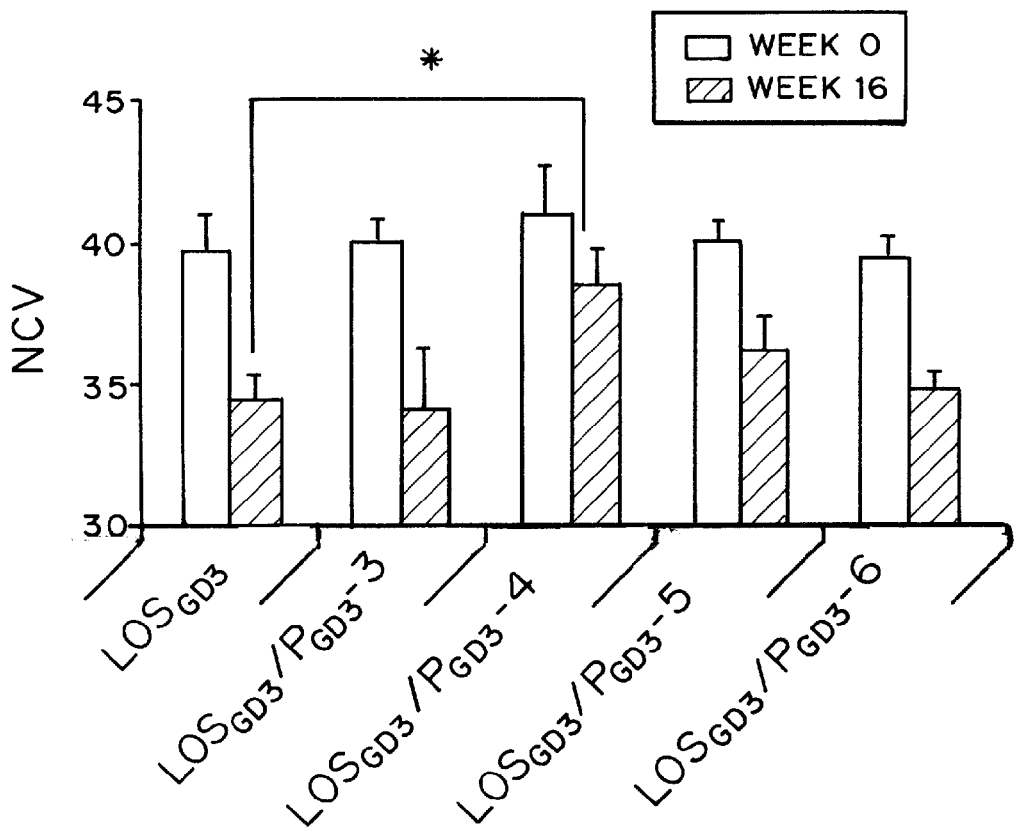
FIGS. 11A-B are bar graphs showing nerve conduction velocity (NCV) (m/sec) at week 0 (open bars) and week 16 (closed bars) after primary immunization by $LOS_{GD3}$ (FIG. 11A, first set of bars), $LOS_{GD3}/P_{GD3}$-3 (FIG. 11A, second set of bars), $LOS_{GD3}/P_{GD3}$-4 (FIG. 11A, third set of bars), $LOS_{GD3}/P_{GD3}$-5 (FIG. 11A, fourth set of bars), $LOS_{GD3}/P_{GD3}$-6 (FIG. 11A, fifth set of bars), Vehicle (FIG. 11B, first set of bars), Vehicle/$P_{GD3}$-3 (FIG. 11B, second set of bars), Vehicle/$P_{GD3}$-4 (FIG. 11B, third set of bars), Vehicle/$P_{GD3}$-5 (FIG. 11B, fourth set of bars), and Vehicle/$P_{GD3}$-6 (FIG. 11B, fifth set of bars).
Figure 11B:
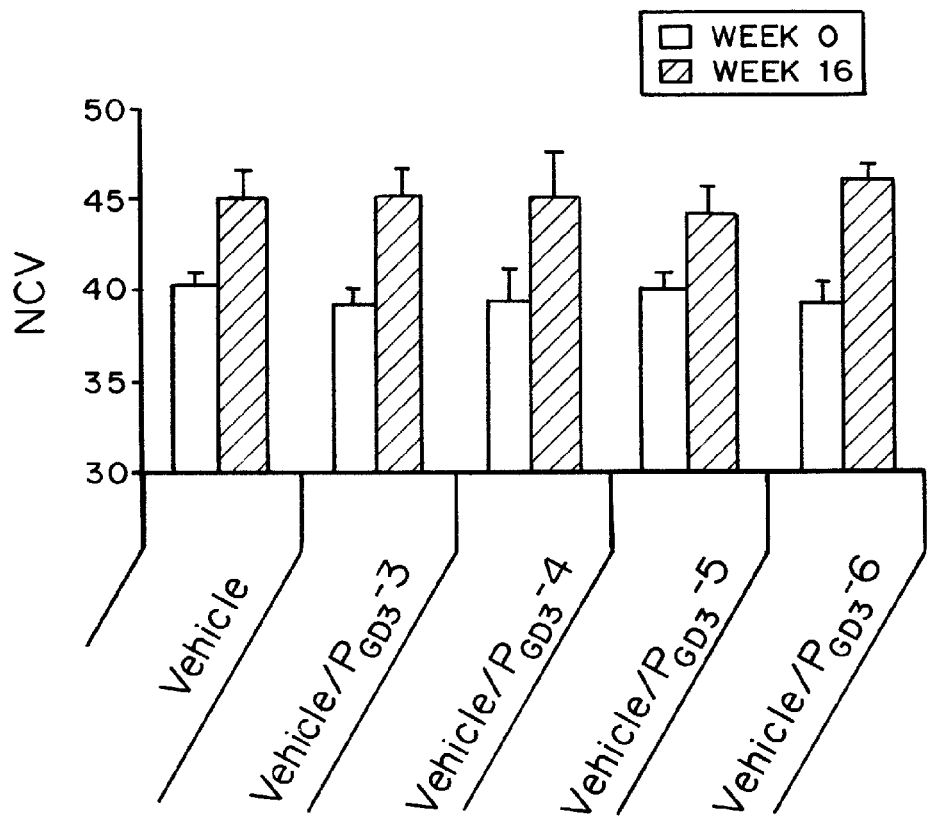

NCVs were measured at week 0 and week 16 post-inoculation. As shown in FIG. 11B, control rats showed slightly increased NCV within the experimental period, presumably because of an age-related change. At week 16, the NCV of the group sensitized by $LOS_{GD3}$ decreased significantly when compared with the corresponding vehicle group (FIG. 11A, p<0.01). Among the $LOS_{GD3}$/peptide-treated groups, $P_{GD3}$-4 and $P_{GD3}$-5 showed less attenuation of NCV, although there was not a statistically significant difference between the treatment and $LOS_{GD3}/P_{GD3}$-5 treatment groups. No change of NCV was observed among the treatment groups with vehicle/peptides (FIG. 11A).

FIGS. 11A-11B shows the effect of treatment of $P_{GD3}$-3, $P_{GD3}$-4, $P_{GD3}$-5, or $P_{GD3}$-6 on NCV with or without $LOS_{GD3}$-treatment. NCVs were measured at week-0 (open square) and at week-16 (closed square) for each of the 10 groups. Assessment of the NCV of the four peptide treatment groups was performed using the immunized groups with $LOS_{GD3}$ and vehicle groups as shown in the upper bar graph: $LOS_{GD3}$, $LOS_{GD3}/P_{GD3}$-3, $LOS_{GD3}/P_{GD3}$-4, $LOS_{GD3}/P_{GD3}$-5, and $LOS_{GD3}/P_{GD3}$-6, and in the lower bar graph: vehicle, vehicle/$P_{GD3}$-3, vehicle/$P_{GD3}$-4, vehicle/$P_{GD3}$-5, and vehicle/$P_{GD3}$-6. Values are mean±SD for four animals. The values were analyzed by One-Way Anova and Dunnet's multiple comparison test (*p<0.01).

Figure 11C:
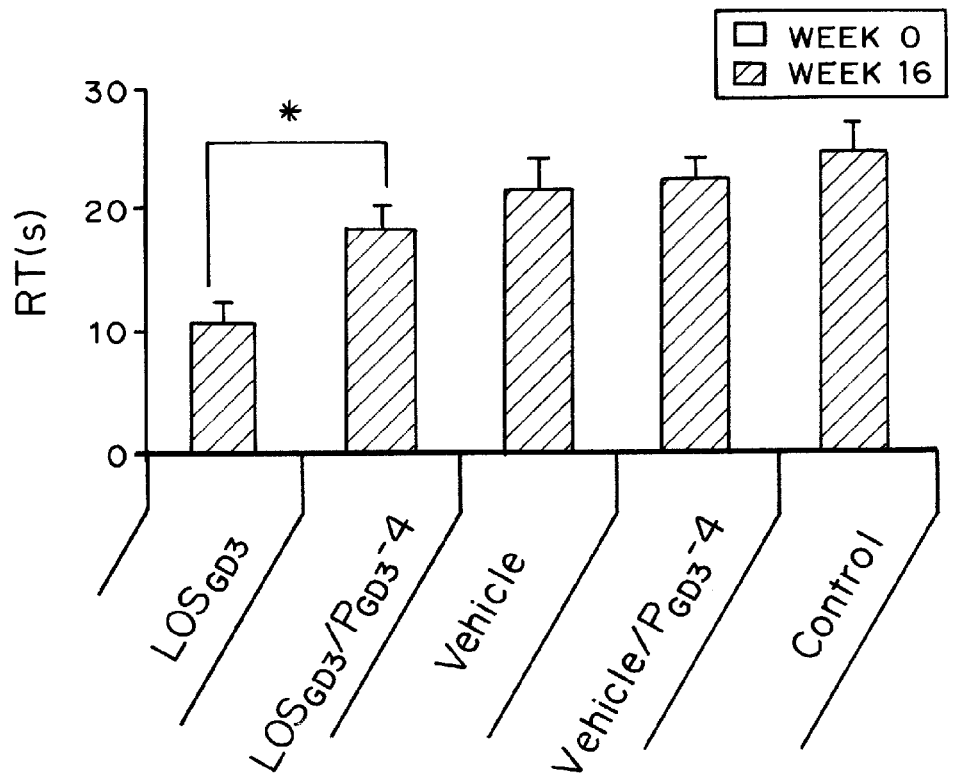
FIG. 11C is a bar graph showing rotarod retention time (sec) 17 weeks after primary immunization by $LOS_{GD3}$ (first bar), $LOS_{GD3}$/BEC2 (second bar), Vehicle (third bar), Vehicle/BEC2 (fourth bar), and Control (fifth bar).

FIG. 11C shows performance of the rotarod test at week-17 after initial sensitization with $LOS_{GD3}$. The graph bars show retention time of rat on the rotating rod. Control group rats maintained balance on the rotating rod at 10 rpm for more than 20 s. The motor disability in $LOS_{GD3}$-treated rats reflected in duration time decreased by 10 s. $P_{GD3}$-4 treatment normalized motor performance with a statistically significant difference from the $LOS_{GD3}$-treated group (*p<0.01).

Figure 11D:
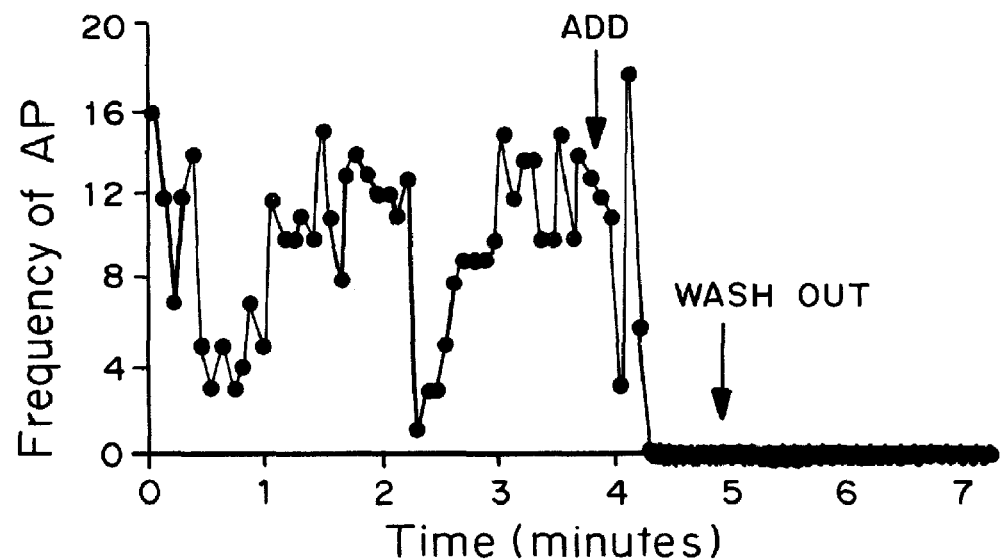
FIGS. 11D-11F are graphs showing spontaneous muscle action potential frequencies (every 5 sec.) in spinal cord-muscle cocultured cells administered serum from rats immunized with $LOS_{GD3}$ (FIG. 11D), $LOS_{GD3}$ (serum subjected to immunoabsorption by GD3) (FIG. 11E), or $LOS_{GD3}/P_{GD3}$-4 (FIG. 11F) as a function of time (min). The arrows show addition of the serum and washing out.
Figure 11E:
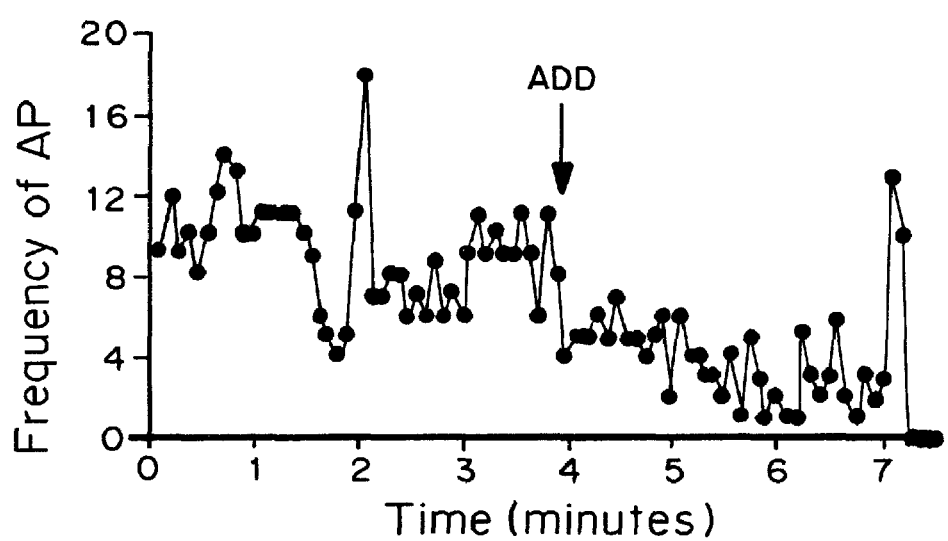
Figure 11F:
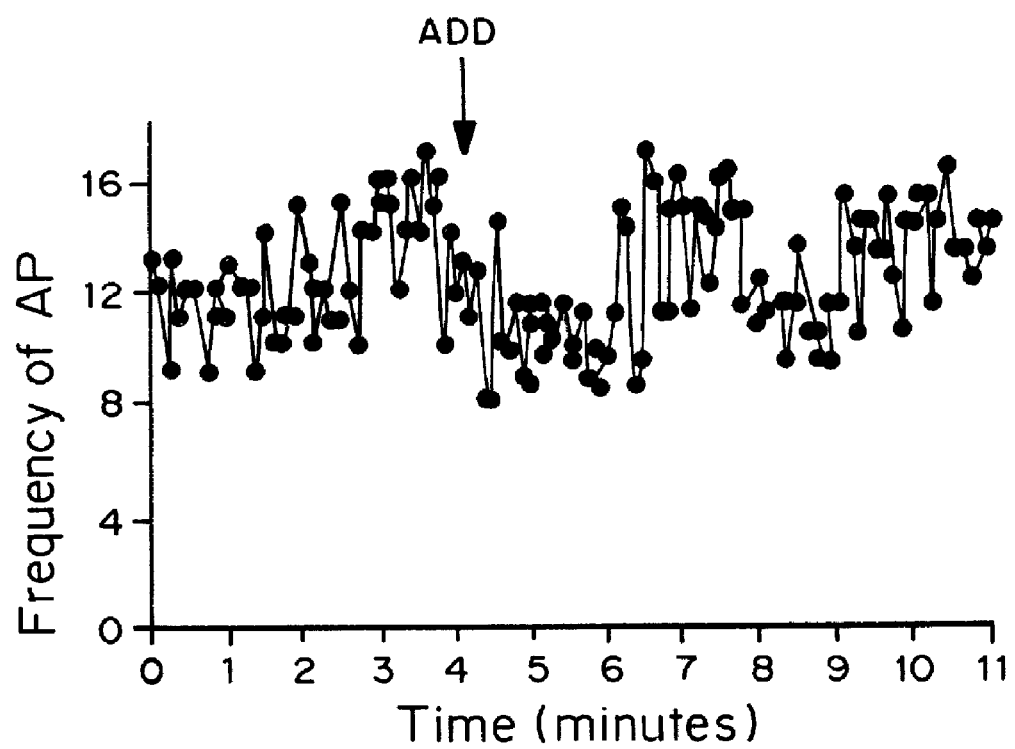

FIGS. 11D-11F show inhibitory effects of rat antisera on muscle action potential frequencies in the spinal cord-muscle co-cultured system. The frequencies were recorded every 5 s. Arrows show addition of 10 µL of rat serum and wash out. Each serum sample of $LOS_{GD3}$ sera and $LOS_{GD3}/P_{GD3}$-4 sera was obtained from four rats at the endpoint of the experiment, respectively, in two groups of $LOS_{GD3}$-treated and $LOS_{GD3}/P_{GD3}$-4-treated animals. Top graph shows effect on muscle action potential after addition of $LOS_{GD3}$ serum; the middle shows that of $LOS_{GD3}$ serum treated by immunoabsorption by GD3. The bottom graph shows the effect on action potential from treatment with $LOS_{GD3}/P_{GD3}$-4, indicating no inhibitory activity in that serum.

Example 16

Rotarod Test

Materials and Methods
Rotarod Motor Test

The rotarod motor test was performed as previously reported (Dunham and Miya, 1957. *J. Am. Pharm. Assoc. Am. Pharm. Assoc.* (Baltim) 46:208-209; Jones and Roberts, 1968. *J. Pharm. Pharmacal.* 20:302-304) and according to the procedure described (Rogers et al., 1997. *Stroke* 28:2060-66).

Results

Animals underwent a rotarod test at week 17, and there was no statistically significant difference in retention time between the vehicle- and untreated-control groups (FIG. 11B). LOS$_{GD3}$-treated animals had muscle weakness and significantly shorter retention times for all of these experimental groups. Among the peptide-treatment groups, a statistically significant difference was found only between the LOS$_{GD3}$/P$_{GD3}$-4 treatment group and the LOS$_{GD3}$ treatment group (p<0.01). The P$_{GD3}$-3, P$_{GD3}$-5, or P$_{GD3}$-6 groups did not show any statistically significant differences following LOS$_{GD3}$ treatment. Similarly, there were no statistically significant differences among the vehicle, vehicle/P$_{GD3}$-4, and control groups.

Example 17

Inhibition of NMJ Activity

Materials and Methods
Neuromuscular Junction (NMJ) Activity

A spinal cord-muscle co-culture was performed as described (Taguchi et al., 2004. *J. Neurol. Sci.* 225:91-98). Briefly, muscle and spinal cord explant cells were prepared from muscle tissue and spinal cord tissue (containing dorsal root ganglia) of 17-day-old fetal rats. Muscle cells and spinal cord explants were co-cultured and maintained for up to 1 week in Dulbecco's modified Eagle's medium supplemented by fetal calf serum and growth factors. Spontaneous muscle action potential frequency was recorded by a glass microelectrode (Ag/AgCl, 30-40 MΩ) and a recording electrode (3 M KCl). The recording system was a Microelectrode Amplifier MEZ-8301, Memory Oscilloscope VC-11 (Nihon Kohden, Tokyo, Japan) and an A-D Converter DigiData 1200 Interface (Axon Instruments, Inc., Union City, Calif., USA). The spontaneous muscle action potential was low-pass filtered at 1 kHz. A rat antiserum solution (10 μL) was delivered directly with a micropipette near the innervated muscle cells.

Results

To determine the nature of the anti-GD3 antibody produced in LOS$_{GD3}$-sensitized rats that manifest neuromuscular weakness, spontaneous muscle action potential frequencies were examined by addition of the serum to a co-culturing system of spinal cord-muscle cells (Usuki et al., 2005. *J. Neurol. Sci.* 232:37-44). Sera from rats sensitized by LOS$_{GD3}$ showed a strong blockade of NMJ action potential frequencies immediately after addition of the serum sample (FIG. 11C, Top). Immunoabsorption [LOS$_{GD3}$ (+absorption)] removed the NMJ blockade; the NMJ action potential, however, did not return to the original frequency level (FIG. 11C, Middle). On the other hand, the LOS$_{GD3}$/P$_{GD3}$-4 serum did not block the NMJ action potential (FIG. 11C, bottom).

Example 18

Morphological Analysis of Motor Neurons and Motor Axons

Materials and Methods
Histological/Morphological Examination

Pathological examination was undertaken to correlate changes with clinical manifestations in the animals. At the endpoint (week 18) of animal experimentation (FIG. 7), the animals were killed. After drawing a blood sample from the heart of each animal, the animals were perfused with 4% paraformaldehyde in PBS buffer via a needle inserted into the arcus aortae. After perfusion, the lumbar spinal cord was dissected and sectioned into 4-6 transverse segments spaced 1 mm apart. The right sciatic nerve was carefully dissected from its origin (5-mm distal to the gluteus maximus) through the distal branch point at the peroneal and tibial nerves and stretching carefully avoided. Nerve sections were placed at 4° C. overnight in a fixative solution containing 4% paraformaldehyde, 2% glutaraldehyde, and 0.1 M sodium cacodylate buffer (pH 7.4). The nerves were washed thrice in cacodylate buffer (pH 7.4), and then post-fixed at 4° C. with 2% osmium tetroxide/0.1 M sodium cacodylate buffer (pH 7.4) for 60 min, dehydrated in graded ethanol, stained at 4° C. with 2% uranyl acetate/70% ethanol for 30 min, and embedded in epoxy resin (Poly/Bed 812, Polysciences, Inc., Warrington, Pa., USA). One-micrometer-thick cross-sections of fascicle were stained with toluidine blue for histological examination using an Axiophot photomicroscope equipped with an Axiocam (Carl Zeiss, Jena, Germany). Images were stored and analyzed using AxioVision. The total number of myelinated fibers in each fascicle was assessed by visual counting, and the myelin to myelinated-area ratio was calculated using Scion Image software (beta 4.0.3). The total fiber area and the total myelin area were marked, and quantitated automatically by the program. Five images were analyzed per cross-section, and the percentage of myelinated area was determined using the following formula: myelin %=(myelinated area/total area)×100.

For electron microscopy, ultra-thin sections were prepared and examined by a high-performance, high-contrast, 40-120 kV transmission electron microscope (JEOL JEM-1230, JEOL Ltd, Tokyo, Japan).

Results

Structural alterations and pathological changes associated with motor spinal cord neurons and sciatic nerves of the LOS$_{GD3}$-treated rats were assessed. Within the lumbar spinal cord, there were no overt structural differences between the anterior horn cells in the untreated control group and the LOS$_{GD3}$-treated group.

Profile counts (numbers of large cells in the anterior horn cross-section) indicated similar densities of lumbar motor neurons in the experimental groups of the control, the LOS$_{GD3}$, and the LOS$_{GD3}$/peptide groups (a, 21±3; b, 26±4; c, 23±4; d, 24±2; e, 25±6; f, 18±6; g, 23±5 neurons/section; n=4, respectively). There were no statistically significant differences among the experimental groups in the neuronal profile area (a, 295±22 μm$^2$; b, 290±22 μm$^2$; c, 252±25 μm$^2$; d, 248±31 μm$^2$; e, 262±25 μm$^2$; f, 288±31 μm$^2$; g, 282±29 μm$^2$; n=4).

To assess morphologic alterations, if any, corresponding to motor dysfunction or muscle weakness evaluated by NCV measurement and rotarod tests, we examined distal motor nerves near the tibial branch of the sciatic nerve; a nerve containing predominantly myelinated motor fibers that serve skeletal muscle fibers of the lower distal leg. Cross-sections of sciatic nerves were prepared and examined by toluidine blue staining and by electron microscopy. Control and vehicle treatments showed normal myelin thickness by both light and electron microscopic examination. The sciatic nerves from the LOS$_{GD3}$-treatment groups manifested obvious axonal destruction, and the remaining axons were surrounded by a very thin myelin sheath with disorganized and disconnected myelin layers. LOS$_{GD3}$/P$_{GD3}$-3, -4, -5, or -6 treatment induced axonal disappearance as a result of destroyed myelin or dissociated myelin debris as shown by light microscopic examination. The LOS$_{GD3}$/P$_{GD3}$-4 treatment group, however, exhibited only a moderate loss of myelinated fibers. Upon ultrastructural examination, myelin-axonal degeneration was commonly found in the LOS$_{GD3}$ treatment and LOS$_{GD3}$/peptide treatment groups as revealed by the presence of empty and enlarged axons surrounded by a very thin myelin sheath.

On the other hand, the LOS$_{GD3}$/P$_{GD3}$-4 treatment group showed a remarkable restoration of myelin thickness.

There was no statistically significant difference in myelin thickness between the control and vehicle groups. A noticeable change of myelin thickness and a statistically significant difference exist, however, in the percentage of myelinated area in the myelinated (i.e. thickness of the average myelin sheath) between the LOS$_{GD3}$ and control/vehicle groups (o, 30±4.2%; p, 31.5±3.2%; q, 11.8±3.8%; $p<0.01$). Among the peptide-treated groups, only the P$_{GD3}$-4 treatment group benefited so that there was no statistical difference in the percentage of myelinated area (r, 30±4.2%; t, 31.5±3.2%; u, 26.8±3.8%).

Example 19

Molecular Docking of GD3-Like Peptides

Materials and Methods
Molecular Docking of GD3-Like Peptides
Conformational analyses of the carbohydrate head group of GD3 and GD3-like peptides were performed using the program Dynamic Molecules. The 3D structure of the B chain of mAb R24 was extracted from the atomic coordinates of PDB code 1r24 using a Swiss-PdbViewer 4.0 (Guex and Peitsch, 1997. *Electrophoresis* 18:2714-2723). Molecular docking was performed using Autodock 3.0 (Morris et al., 1996. *J. Comput. Aided Mol. Des.* 10:293-304), and the docking results were collated by MGL Tools (Sanner, 1999. *J. Mol. Graph. Model* 17:57-61) or PyMOL (DeLano Scinetific, Palo Alto, Calif.).

Results

In this study, the tetrasaccharide head group of ganglioside GD3 was found to dock into the binding pocket of mAb R24 that is formed by the complementarity-determining regions (CDRs): CDR1, 2, and 3 with a docking energy of −4.2 kcal/mol. Our data indicate that CDR2 binds the galactose and glucose residues and that CDR3 has a role anchoring the two sialic acid residues. P$_{GD3}$-1 and PG$_{GD3}$-2 failed to dock into the binding pocket on the B chain of mAb R24, while peptides P$_{GD3}$-3, P$_{GD3}$-4, P$_{GD3}$-5, and P$_{GD3}$-6 successfully docked into the binding pocket with docking energies from −3.5 to −4.5 kcal/mol.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

We claim:

1. A method of treating Guillain-Barré syndrome (GBS) in a subject, comprising administering to the subject an effective amount of a pharmaceutical composition comprising a polypeptide comprising a GD3 ganglioside epitope of SEQ ID NO:4.

2. The method of claim 1, wherein the polypeptide comprising a ganglioside epitope is an anti-idiotypic antibody.

3. The method of claim 1, wherein the GD3 ganglioside epitope of SEQ ID NO:4 mimics a GD3 ganglioside comprising NeuAcα2-8NeuAcα2-3Galβ1-4Glcβ1-1'Cer.

* * * * *